US007951583B2

(12) United States Patent
Duer

(10) Patent No.: US 7,951,583 B2
(45) Date of Patent: May 31, 2011

(54) OPTICAL SCANNING SYSTEM

(75) Inventor: Reuven Duer, Thousand Oaks, CA (US)

(73) Assignee: PLC Diagnostics, Inc., Thousand Oaks, CA (US)

( * ) Notice: Subject to any disclaimer, the term of this patent is extended or adjusted under 35 U.S.C. 154(b) by 1117 days.

(21) Appl. No.: 11/683,808

(22) Filed: Mar. 8, 2007

(65) Prior Publication Data
US 2007/0211985 A1    Sep. 13, 2007

Related U.S. Application Data

(60) Provisional application No. 60/743,458, filed on Mar. 10, 2006.

(51) Int. Cl.
*C12M 3/00* (2006.01)
*C12M 1/34* (2006.01)

(52) U.S. Cl. .......................... 435/288.7; 385/12; 385/14

(58) Field of Classification Search .................. 435/6, 288.5–288.7; 422/82.08, 422/82.11; 385/12, 14
See application file for complete search history.

(56) References Cited

U.S. PATENT DOCUMENTS

| | | | |
|---|---|---|---|
| 4,394,060 A * | 7/1983 | Verber et al. ................ 385/7 |
| 4,478,485 A | 10/1984 | Khoe et al. |
| 4,515,430 A | 5/1985 | Johnson |
| 4,744,623 A | 5/1988 | Prucnal et al. |
| 4,746,179 A | 5/1988 | Dahne et al. |
| 4,799,797 A | 1/1989 | Huggins |
| 4,815,843 A | 3/1989 | Tiefenthaler et al. |
| 4,820,016 A | 4/1989 | Cohen et al. |
| 4,850,666 A | 7/1989 | Izutsu et al. |
| 4,876,446 A | 10/1989 | Kambe et al. |
| 4,881,789 A | 11/1989 | Levinson |
| 4,889,407 A | 12/1989 | Markle et al. |
| 4,906,837 A | 3/1990 | Doneen et al. |
| 4,940,328 A | 7/1990 | Hartman |
| 4,978,503 A | 12/1990 | Shanks et al. |
| 5,031,987 A | 7/1991 | Norling |
| 5,077,878 A | 1/1992 | Armiento et al. |
| 5,121,457 A | 6/1992 | Foley et al. |

(Continued)

FOREIGN PATENT DOCUMENTS

EP    0737308 B1    3/1998

(Continued)

OTHER PUBLICATIONS

Ausubel, et al. (Eds.) Cu'rrent Protocols in Molecular Biology, vols. I, II, and III, (1997).

(Continued)

*Primary Examiner* — Walter D Griffin
*Assistant Examiner* — Shanta G Doe
(74) *Attorney, Agent, or Firm* — Arnold & Porter LLP; Ginger R. Dreger

(57) ABSTRACT

A scanning sensor system 100, methods and kits for use thereof including a switchable light source 102, a detector 106, a substrate 104 and a plurality of optical sensing sites 112 are provided. Substrate 104 is coupled to and in optical communication with switchable light source 102 and detector 106. Additionally, substrate 104 includes a plurality of substantially parallel excitation waveguides 108, and a plurality of substantially parallel collection waveguides 110, the excitation waveguides 108 and collection waveguides 110 crossing to form a two-dimensional array and optical communication with intersection regions 114 at each crossing. The plurality of optical sensing sites 112 are each in optical communication with an intersection region 114.

69 Claims, 22 Drawing Sheets

U.S. PATENT DOCUMENTS

| | | | |
|---|---|---|---|
| 5,173,747 A | 12/1992 | Boiarski et al. | |
| 5,217,568 A | 6/1993 | Tessier et al. | |
| 5,344,784 A | 9/1994 | Attridge | |
| 5,377,008 A | 12/1994 | Ridgway et al. | |
| 5,439,647 A | 8/1995 | Saini | |
| 5,444,805 A | 8/1995 | Mayer | |
| 5,455,178 A | 10/1995 | Fattinger | |
| 5,479,260 A | 12/1995 | Fattinger | |
| 5,494,798 A | 2/1996 | Gerdt et al. | |
| 5,496,701 A | 3/1996 | Pollard-Knight | |
| 5,512,492 A | 4/1996 | Herron et al. | |
| 5,547,839 A | 8/1996 | Dower et al. | |
| 5,573,956 A | 11/1996 | Hanning | |
| 5,577,137 A | 11/1996 | Groger et al. | |
| 5,581,646 A | 12/1996 | Tsukamoto et al. | |
| 5,585,639 A * | 12/1996 | Dorsel et al. | 250/458.1 |
| 5,600,744 A | 2/1997 | Takahashi | |
| 5,623,561 A | 4/1997 | Hartman | |
| 5,640,234 A | 6/1997 | Roth et al. | |
| 5,650,123 A | 7/1997 | Saini et al. | |
| 5,671,303 A | 9/1997 | Shieh et al. | |
| 5,677,196 A | 10/1997 | Herron et al. | |
| 5,677,769 A | 10/1997 | Bendett | |
| 5,710,000 A | 1/1998 | Sapolsky et al. | |
| 5,712,937 A | 1/1998 | Asawa et al. | |
| 5,734,768 A | 3/1998 | Kim et al. | |
| 5,737,457 A | 4/1998 | Saini et al. | |
| 5,800,992 A | 9/1998 | Fodor et al. | |
| 5,814,565 A | 9/1998 | Reichert et al. | |
| 5,822,472 A | 10/1998 | Danielzik et al. | |
| 5,830,766 A | 11/1998 | Attridge et al. | |
| 5,832,165 A | 11/1998 | Reichert et al. | |
| 5,841,914 A | 11/1998 | Shieh et al. | |
| 5,846,842 A | 12/1998 | Herron et al. | |
| 5,861,242 A | 1/1999 | Chee et al. | |
| 5,919,712 A | 7/1999 | Herron et al. | |
| 5,961,924 A | 10/1999 | Reichert et al. | |
| 6,027,880 A | 2/2000 | Cronin et al. | |
| 6,108,463 A | 8/2000 | Herron et al. | |
| 6,110,749 A | 8/2000 | Obremski et al. | |
| 6,141,465 A | 10/2000 | Bischel et al. | |
| 6,222,619 B1 | 4/2001 | Herron et al. | |
| 6,228,575 B1 | 5/2001 | Gingeras et al. | |
| 6,287,871 B1 | 9/2001 | Herron et al. | |
| 6,316,274 B1 | 11/2001 | Herron et al. | |
| 6,340,598 B1 | 1/2002 | Herron et al. | |
| 6,350,413 B1 | 2/2002 | Reichert et al. | |
| 6,361,947 B1 | 3/2002 | Dong et al. | |
| 6,384,912 B2 | 5/2002 | Kraus et al. | |
| 6,389,186 B1 | 5/2002 | DiGiovanni et al. | |
| 6,395,558 B1 | 5/2002 | Duveneck et al. | |
| 6,396,995 B1 | 5/2002 | Stuelpnagel et al. | |
| 6,465,241 B2 | 10/2002 | Haronian et al. | |
| 6,483,096 B1 | 11/2002 | Kunz et al. | |
| 6,498,041 B1 | 12/2002 | Tabacco et al. | |
| 6,611,634 B2 | 8/2003 | Herron et al. | |
| 6,618,536 B1 | 9/2003 | Heideman et al. | |
| 6,661,938 B2 | 12/2003 | Lim et al. | |
| 6,759,663 B2 | 7/2004 | Tsipouras et al. | |
| 6,785,432 B2 | 8/2004 | Letant et al. | |
| 6,801,677 B1 | 10/2004 | Grace et al. | |
| 6,830,936 B2 * | 12/2004 | Anderson et al. | 436/180 |
| 6,847,746 B2 | 1/2005 | Uchiyama | |
| 6,911,344 B1 | 6/2005 | Reichert et al. | |
| 6,947,634 B2 | 9/2005 | Tanaka et al. | |
| 6,956,651 B2 | 10/2005 | Lackritz et al. | |
| 6,974,673 B2 | 12/2005 | Lockhart | |
| 6,979,567 B2 | 12/2005 | Herron et al. | |
| 6,987,898 B2 | 1/2006 | Tran et al. | |
| 7,175,811 B2 | 2/2007 | Bach et al. | |
| 7,292,336 B2 | 11/2007 | Cunningham et al. | |
| 7,349,080 B2 | 3/2008 | Aklian | |
| 7,708,945 B1 * | 5/2010 | Abel et al. | 422/58 |
| 2001/0001021 A1 | 5/2001 | Kraus et al. | |
| 2002/0097947 A1 | 7/2002 | Lim et al. | |
| 2002/0114576 A1 | 8/2002 | Schroeder | |
| 2002/0126936 A1 | 9/2002 | Lockhart | |
| 2002/0126938 A1 | 9/2002 | Lockhart | |
| 2002/0172457 A1 | 11/2002 | Tapalian et al. | |
| 2002/0191884 A1 | 12/2002 | Letant et al. | |
| 2002/0197456 A1 | 12/2002 | Pope | |
| 2003/0059853 A1 | 3/2003 | Lockhart | |
| 2003/0063851 A1 | 4/2003 | Hillendahl et al. | |
| 2003/0108291 A1 | 6/2003 | Duveneck et al. | |
| 2003/0138208 A1 | 7/2003 | Pawlak et al. | |
| 2003/0169956 A1 | 9/2003 | Lange et al. | |
| 2004/0008919 A1 | 1/2004 | Freeman et al. | |
| 2004/0022475 A1 | 2/2004 | Pennington | |
| 2004/0023396 A1 | 2/2004 | Boyd et al. | |
| 2004/0052489 A1 | 3/2004 | Duveneck et al. | |
| 2004/0081384 A1 | 4/2004 | Datesman et al. | |
| 2005/0078903 A1 | 4/2005 | Grace et al. | |
| 2005/0088648 A1 | 4/2005 | Grace et al. | |
| 2005/0089261 A1 | 4/2005 | Shimazaki | |
| 2005/0145783 A1 | 7/2005 | Zheng | |
| 2005/0153320 A1 | 7/2005 | Herron et al. | |
| 2005/0195394 A1 | 9/2005 | Ma et al. | |
| 2005/0201657 A1 | 9/2005 | Tiefenthaler | |
| 2005/0201659 A1 | 9/2005 | Strecker | |
| 2005/0254744 A1 | 11/2005 | Freeman | |
| 2006/0008227 A1 | 1/2006 | Schmidt et al. | |
| 2006/0014151 A1 | 1/2006 | Ogura et al. | |
| 2006/0061754 A1 | 3/2006 | Turner et al. | |
| 2006/0078889 A1 * | 4/2006 | Bhattacharjee et al. | 435/6 |
| 2006/0098927 A1 | 5/2006 | Schmidt et al. | |
| 2006/0183145 A1 | 8/2006 | Turner | |
| 2007/0231458 A1 | 10/2007 | Gale | |
| 2007/0231880 A1 | 10/2007 | Chang-Yen | |
| 2009/0068668 A1 | 3/2009 | Duer | |
| 2009/0312188 A1 | 12/2009 | Duer et al. | |

FOREIGN PATENT DOCUMENTS

| | | | |
|---|---|---|---|
| EP | 0783683 B1 | | 4/2004 |
| EP | 1413876 A2 | | 4/2004 |
| EP | 1441217 A2 | | 7/2004 |
| EP | 1413876 A3 | | 2/2005 |
| EP | 1441217 A3 | | 7/2007 |
| GB | 2377492 | * | 1/2003 |
| WO | WO 92/21768 A1 | | 12/1992 |
| WO | WO 94/18544 A1 | | 8/1994 |
| WO | WO 94/28395 A1 | | 12/1994 |
| WO | WO 95/14225 A1 | | 5/1995 |
| WO | WO 95/33197 A1 | | 12/1995 |
| WO | WO 95/33198 A1 | | 12/1995 |
| WO | WO 97/39370 A1 | | 10/1997 |
| WO | WO 99/45354 A2 | | 9/1999 |
| WO | WO 99/45354 A3 | | 10/1999 |
| WO | WO 00/75644 A1 | | 12/2000 |
| WO | WO/01/13096 | * | 8/2001 |
| WO | WO 02/066983 A2 | | 8/2002 |
| WO | WO 03/006625 A2 | | 1/2003 |
| WO | WO 02/066983 A3 | | 5/2003 |
| WO | WO 03/062791 A2 | | 7/2003 |
| WO | WO 2004/020987 A1 | | 3/2004 |
| WO | WO 03/062791 A3 | | 6/2004 |
| WO | WO 2005/043139 A1 | | 5/2005 |
| WO | WO 2005/084367 A2 | | 9/2005 |
| WO | WO 2006/135782 A2 | | 12/2006 |
| WO | WO 2007/070869 A2 | | 6/2007 |
| WO | WO 2008/069973 A2 | | 6/2008 |

OTHER PUBLICATIONS

Ausubel, et al. (Eds.), Short Protocols in Molecular Biology: A Compendium of Methods from Current Protocols in Molecular Biology, 5th Ed., John Wiley & Sons, Inc. (2002).

Batzer, et al. Enhanced evolutionary PCR using oligonucleotides with inosine at the 3'-terminus. *Nucleic Acid Res. 1991*; 19:5081.

Chee, et al. Accessing genetic information with high density DNA arrays. Science. 1996; 274:610-614.

Herron, et al. Orientation and Activity of Immobilized Antibodies. In: Biopolymers at Interfaces, 2nd Edition (M. Malmsten, ed.). Surfactant Science Series. Marcel Dekker, New York. 2003; 110:115-163.

Herron, et al. Planar waveguide biosensors for point-of-care clinical and molecular diagnostics. In: Fluorescence Sensors and Biosensors. R. B. Thompson, Ed. CRC Press Taylor & Francis Group. Boca Raton, FL. 2005: 283-332.

Innis, et al. (Eds.) PCR Protocols: A Guide to Methods and Applications, Elsevier Science & Technology Books (1990).

Kreuzer, et al. LightCycler technology for the quantitation of bcr/abl fusion transcripts. Cancer Research. 1999; 59(13):3171-4.

Laurendeau, et al. Quantitation of MYC gene expression in sporadic breast tumors with a real-time reverse transcription-PCR assay. Clin Chem. 1999; 59(12):2759-65.

Laurendeau, et al. TaqMan PCR-based gene dosage assay for predictive testing in individuals from a cancer family with INK4 locus haploinsufficiency. Clin Chem. 1999; 45(7):982-6.

Ohtsuka, et al. An alternative approach to deoxyoligonucleotides as hybridization probes by insertion of deoxyinosine at ambiguous codon positions. *J. Biol. Chem. 1985*; 260:2605-2608.

Rossolini, et al. Use of deoxyinosine-containing primers vs degenerate primers for polymerase chain reaction based on ambiguous sequence information. *Mol. Cell. Probes. 1994*; 8:91-98.

Saizieu, et al. Bacterial transcript imaging by hybridization of total RNA to oligonucleotide arrays. Nat Biotechnol. 1998; 16(1):45-8.

Sambrook, et al., Molecular Cloning: A Laboratory Manual, 3rd Ed., Cold Spring Harbor Laboratory Press (2000).

Bieche, et al. Quantitation of MYC gene expression in sporadic breast tumors with a real-time reverse transcription-PCR assay. Cancer Res. Jun. 15, 1999;59(12):2759-65.

\* cited by examiner

OPTICAL SCANNING SYSTEM

CROSS-REFERENCE

This application claims the benefit of U.S. Provisional Application No. 60/743,458, filed Mar. 10, 2006 entitled Optical Scanning System, which is incorporated herein by reference in its entirety.

BACKGROUND OF THE INVENTION

Biological substance analysis methods based on optical means have risen in popularity in the last couple of decades. Common to all these methods is that chemical interactions between the bio-molecules produce changes that affect some measurable optical properties, such as emission spectrum, absorption spectrum and index of refraction. The changes in the optical properties can occur in the analyte itself or through a mediator such as the surface on which the interaction takes place. These changes are then monitored using a beam of incoming light (usually laser light) which in-turn changes the outgoing light spectrum (e.g. in fluorescence), intensity (e.g. in absorption), or phase (e.g. Surface Plasmon Resonance=SPR and any kind of interferometric method).

While most of these optical bio-analysis methods have found niche applications and markets, one method that became highly popular and influential was microarray optical fluorescence scanning. Such optical scanning has enabled running tests on tens of thousands of miniature samples in a relatively short period of time. The major advantages of this method include: a) performance (sensitivity & Signal to Noise Ratio=SNR); b) speed; and c) miniaturization of the sampled analyte. These parameters define the efficiency and superiority of the method.

Currently microarray elements are spotted on top of a flat substrate chip usually made of glass, plastic or epoxy. Subsequently, the chip is scanned using confocal scanning systems where the exciting light and the resulting fluorescence light are both shined and collected from above and analyzed using a single photo-multiplier (PMT) detector. This arrangement suffers from several inherent limitations including a very short interaction length between the bio-sample and the light (usually a single mono-layer). This limits the signal strength and thus the SNR. Another limitation is a high background or noise due to the fact that the back reflected light and the emitted fluorescent light travel in the same direction. A further limitation is high sensitivity to the planarity and the position of the chip that need to be maintained in focus. Still another limitation is slow operation due to the need to have large enough number of 'pixels' (scanned spots) within every sample and long enough integration time. Yet another limitation is the need for a complicated optical and mechanical structure that entails bulky and expensive systems.

Another optical bio-analysis method is waveguide based bio-sensors. Bio-sensing based on waveguides has been around for a while. These biosensors can be divided into three main categories. The first involve slab waveguide fluorescence excitation with light collection from above or below the chip. In this arrangement the bio-analyzed spots are located on the surface of a chip that contains a single slab-waveguide. Light is coupled into the waveguide using a lens or a grating that excites the entire chip with all its bio-analyzed spots simultaneously. The fluorescence is collected using an optical imaging system and a Charge-Coupled Device (CCD) detector from above or underneath the chip. One drawback of this kind of systems is relatively poor performance due to uniformity of excitation as well as collection of the light. This leads to non-repeatable results. Another drawback is high noise levels due to crosstalk between the different spots. A further drawback is that large spots and relatively small numbers of elements are required to generate signal large enough for efficient imaging with the CCD. Yet another drawback is the long integration time to overcome SNR issues. Examples of the above method are described in U.S. Pat. Nos. 5,814,565; 6,911,344 and 6,395,558.

A second waveguide based bio-sensor utilizes an interferometric optical device. In this case, channel waveguides are used together with interferometric devices such as Mach Zehender Interferometers (MZI) or ring-resonators. These sensitive interferometric devices sense the change in the index of refraction due to binding of the bio-molecules near a waveguide surface. The major problems associated with this type of systems include non-specificity due to inability to recognize the exact reason for the index change which may occur from other material deposition as well as temperature changes. Another problem is a very slow speed in addressing the different elements which disqualify this method for running large numbers of element arrays. Examples of the above method are described in U.S. Pat. Nos. 5,494,798, 4,515,430, 5,623,561 and 6,618,536.

A third waveguide based bio-sensor utilizes Surface Plasmon Resonance (SPR). Here, in one example, a thin gold layer deposited on top of a glass substrate. The bio-analyzed sample on top of the gold induces changes in the refractive index above the gold layer and thus changing the resonant angle for generating surface Plasmons along the gold layer. The Plasmons generation is detected as an enhanced peak in the reflected beam. Examples of the SPR method are covered, for example, in U.S. Pat. No. 6,956,651 B2. Other types of optical bio-sensors and array scanners exist such as U.S. Pat. No. 6,396,995 B1.

SUMMARY OF THE INVENTION

In general, in one aspect, the invention features a scanning sensor system, methods and kits for use thereof including a switchable light source, a detector, a substrate and a plurality of optical sensing sites. The substrate is coupled to and in optical communication with the switchable light source and the detector. Additionally, the substrate includes a plurality of substantially parallel excitation waveguides, and a plurality of substantially parallel collection waveguides, the excitation waveguides and collection waveguides crossing to form a two-dimensional array and optical communication with inter-section regions. The plurality of optical sensing sites are each in optical communication with an intersection region.

Implementations of the invention can include one or more of the following features.

In one aspect of the invention a scanning sensor system for detecting a biologically active analyte is provided. The system includes a switchable light source, a detector and a substrate coupled to and in optical communication with the switchable light source and the detector. The substrate includes a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing. The system further includes a plurality of optical sensing sites each in optical communication with an intersection region.

In one embodiment, the system is substantially planar. In a particular embodiment the system includes a planar lightwave circuit.

In another embodiment the switchable light source is coupled to and in communication with one or more of the excitation waveguides at a first edge of the substrate and the detector is coupled to and in communication with one or more of the collection waveguides at a second edge of the substrate.

In one embodiment the optical sensing sites include a sensor including a biologically active analyte in a sample, and wherein a measurable change in the first light wave results when the sensor discriminates or interacts with the biologically active analyte.

In one embodiment of the system a first light wave generated by the switchable light source in an excitation waveguide is transduced by a sensor of an optical sensing site in optical communication with the excitation wave guide resulting in a second light wave in a collection waveguide, the second light wave being detectable by the detector.

In another embodiment of the system the sensor is adapted to support an immunoassay. In a particular embodiment the immunoassay supported is an enzyme-linked immunosorbent assay (ELISA). In another embodiment the immunoassay supported is a fluorescent immunoassay. In yet another embodiment the sensor is selected from a fluorescence well, an absorption cell, an interferometric sensor, a diffractive sensor and a surface plasmon resonance sensor.

In one embodiment of the system the biologically active analyte is selected from a nucleic acid, a protein, an antigen, an antibody, a microorganism, a gas, a chemical agent and a pollutant. In a particular embodiment the nucleic acid is produced via an amplification reaction.

In one embodiment of the system the excitation waveguides are single-mode and the collection waveguides are multi-mode. In another embodiment the excitation waveguides support single-mode in a first vertical dimension and multi-mode in a second lateral dimension and wherein the collection waveguides are multi-mode. In a further embodiment the excitation waveguides and the collection waveguides are multi-mode. In another embodiment the excitation waveguides and the collection waveguides are single-mode. In yet another embodiment the excitation waveguide comprises a plurality of branches for drawing a fraction of the light from a first light wave traveling in the excitation waveguide. In a related embodiment the excitation waveguide branches are in optical communication with the excitation waveguide.

In one embodiment of the system the collection waveguide include a plurality of funnels for collecting light from the sensing sites and coupling it to the collection waveguide. In a particular embodiment the optical sensing sites comprise wells. In one embodiment the optical sensing sites include the surface of the substrate above the intersection region of the excitation waveguides and the collection waveguides. In another embodiment the optical sensing sites include biochemical interaction sites. In a further embodiment the optical sensing sites include optical transducers. In one embodiment the optical transducers include fluorescence wells comprising fluorescent or luminescent compounds, wherein light waves guided by the excitation waveguides excite the fluorescent or luminescent compound in the wells in the presence of a biologically active analyte, and the collection waveguides collect and guide light emitted from the wells to the detector.

In one embodiment of the system the switchable light source includes a dynamic light source. In one embodiment the switchable light source includes a chip containing an array of light generators coupled to an array of waveguides. In another embodiment the switchable light source is an optical switch including a light generator coupled to one or more input of the optical switch. In a particular embodiment the optical switch further includes a branched architecture. In one embodiment the optical switch further includes one or more inputs and multiple outputs. In another embodiment the optical switch further includes greater than about 10 outputs. In yet another embodiment the optical switch further includes greater than about 100 outputs. In a further embodiment the optical switch further includes greater than about 1,000 outputs. In one embodiment the optical switch further includes substantially between 50 and 500 outputs. In another embodiment the switchable light source is butt-coupled to the substrate. In yet another embodiment the switchable light source includes one or more waveguide and is evanescently coupled to the substrate through a proximate arrangement of the one or more switchable light source waveguide and one or more excitation waveguide of the substrate.

In one embodiment of the system the light generator provides variable wavelengths of light. In another embodiment the light generator is selected from the group consisting of a broad-band source, a source with one or more discrete spectral lines and a tunable source.

In one embodiment of the system the detector is a photodetector array. In a particular embodiment the detector is a plurality of detectors. In one embodiment two or more detectors are coupled to and in optical communication with one or more of the collection waveguides or the excitation waveguides at one or more edges of the substrate.

In one embodiment of the system the number of intersection regions is greater than 10. In another embodiment the density of intersection regions is greater than 100 per $cm^2$. In yet another embodiment the density of intersection regions is greater than 2,000 per $cm^2$.

One embodiment of the system further includes a thermal transfer element in thermal communication with the substrate. In a particular embodiment the thermal transfer element is a thermoelectric cooler. In one embodiment each optical sensing site includes a thermal transfer element in thermal communication with the optical sensing site. In another embodiment the thermal transfer element includes a thin-film heater. In one embodiment each optical sensing site further includes a thermistor in thermal communication with the optical sensing site.

In one embodiment of the system the substrate further includes one or more microchannel and one or more reservoirs in fluid communication with one or more optical sensing site. In one embodiment the system further includes a fluidics layer coupled to the substrate and comprising one or more microchannel and one or more reservoirs in fluid communication with one or more optical sensing site.

In another aspect the invention provides scanning sensing method including delivering a sample suspected of containing a biologically active analyte to be detected to an optical sensing site of a scanning sensor system, providing a first light wave using a switchable light source to one or more of a plurality of substantially parallel excitation waveguides in optical communication with the optical sensing site, wherein the first light wave is transducable by a sensor associated with the optical sensing site to a second light wave carried in one or more of a plurality of substantially parallel collection waveguides in optical communication with the optical sensing site and crossing the excitation waveguides. The method further includes detecting a measurable change in the second light wave using a detector in optical communication with the collection waveguides, wherein a measurable change in the first light waves occurs when the sensor interacts with the biologically active analyte.

In one embodiment scanning sensing further includes switching one or more input light wave from the switchable light source into the substrate to produce the first light wave in one or more of the excitation waveguides. In a particular embodiment the switchable light source includes an optical switch for controlled switching of one or more input light wave, the optical switch can multicast light to a plurality of outputs and into the substrate to controllably produce the first light wave in one or more of the excitation waveguides. In one embodiment the switchable light source includes an array of individually controlled light generators for controlled switching of one or more input light wave, to controllably produce the first light wave in one or more of the excitation waveguides.

In one embodiment scanning sensing further includes simultaneously detecting the second light wave with the detector at the end of each collection waveguide wherein the detector comprises a photodetector array. In one embodiment a portion of the sensing sites include reference sample material for calibration and/or normalization.

In one embodiment the biologically active analyte is selected from a nucleic acid, a protein, an antigen, an antibody, a microorganism, a gas, a chemical agent and a pollutant. In a particular embodiment the biologically active analyte is a protein. In one embodiment a SNP is detected in the biologically active analyte. In another embodiment expression of a gene is detected upon detection of the biologically active analyte.

In one embodiment the sensor of the scanning sensing method is adapted to support an immunoassay and the sensor interacting with the biologically active analyte includes an outcome of an immunoassay. In one embodiment the immunoassay supported is an enzyme-linked immunosorbent assay (ELISA). In another embodiment the immunoassay supported is a fluorescent immunoassay.

In one embodiment of the method detecting a measurable change in the second lightwave provides a diagnostic result. In another embodiment the method includes conducting a real-time PCR reaction at the optical sensing site.

In one aspect the invention provides a kit for assaying a sample for a biologically active analyte including a scanning sensor system comprising a switchable light source, a detector, and a substrate coupled to and in optical communication with the switchable light source and the detector. The substrate includes a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection regions at each crossing, and a plurality of optical sensing sites each in optical communication with an intersection region. The kit also includes packaging and instructions for use of the system. In one embodiment the system includes a planar lightwave circuit. In another embodiment crossings of the excitation waveguides and collection waveguides are substantially perpendicular. In a particular embodiment the optical sensing sites include a sensor adapted to support an immunoassay, and the kit further includes one or more immunoassay reagents.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE FIGURES

A better understanding of the features and advantages of the present methods and compositions may be obtained by reference to the following detailed description that sets forth illustrative embodiments, in which the principles of our methods, compositions, devices and apparatuses are utilized, and the accompanying drawings of which.

DETAILED DESCRIPTION OF THE INVENTION

Figure 1A:
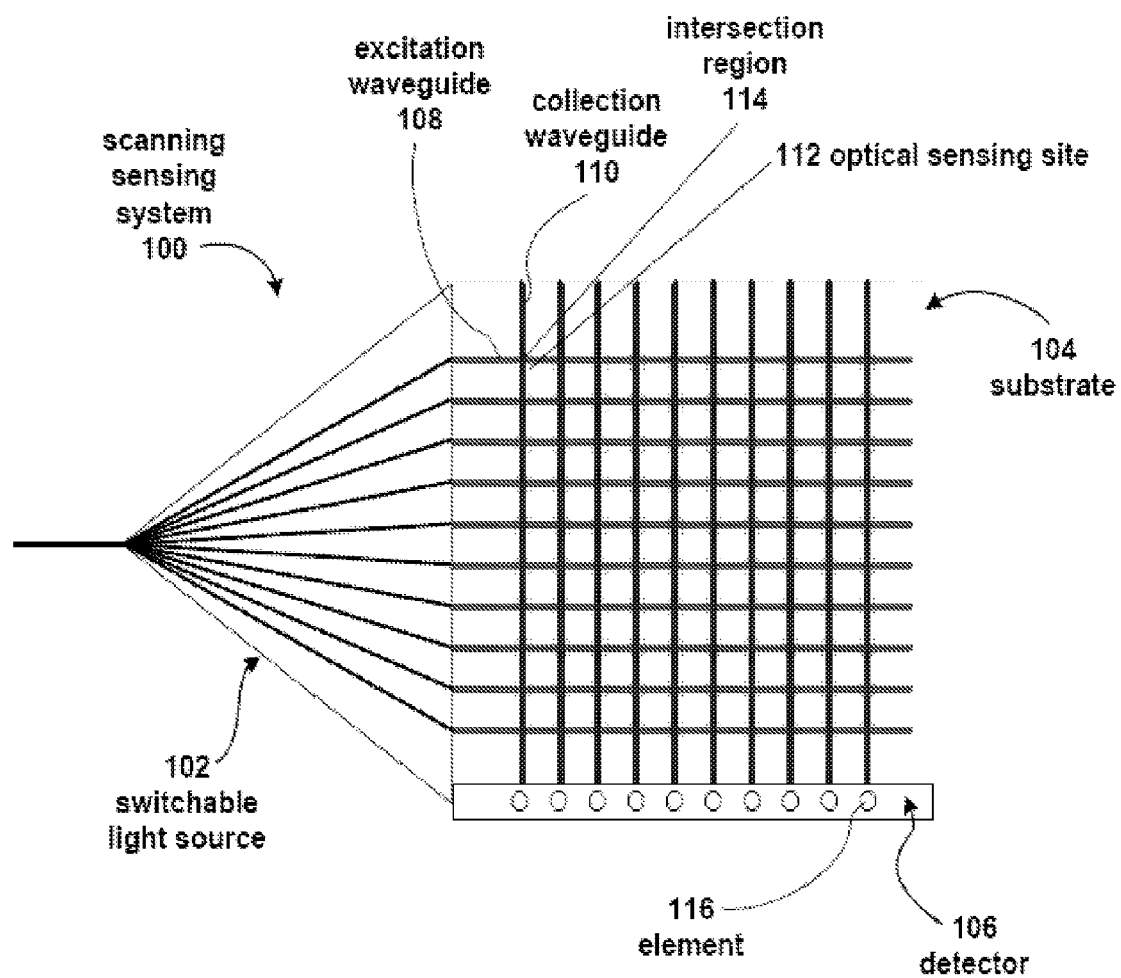
FIG. 1A is a schematic of the scanning sensing system of the invention including a switchable light source, a substrate, a detector and optical sensing sites.

Apparatus, methods, and kits for optical sensing, using a scanning sensing system including a switchable light source, a detector a substrate and a plurality of optical sensing sites are provided. The substrate of the system includes a plurality of substantially parallel excitation waveguides and a plurality of substantially parallel collection waveguides. The excitation waveguides and collection waveguides cross to form an intersection region and a two-dimensional array. The optical sensing sites include a sensor and are in optical communication with one or more excitation waveguides and one or more collection waveguides. Sensing of a variety of environmental and biological samples can be achieved using the apparatus, methods and kits described herein. The general theoretical principles of lightwave guiding and evanescent field fluorescence excitation apply to the embodiments disclosed herein.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

Definitions

The term "biologically active analyte" when used herein means any substance which can affect any physical or biochemical properties of a biological organism, including but not limited to viruses, bacteria, fungi, plants, animals, and humans. In particular as used herein, biologically active analyte according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, gene, protein, or hormone, or any combination thereof. A biologically active analyte can further include a natural or man-made substance including but not limited to a gas, a chemical agent or a pollutant, or a combination thereof (e.g., from an environmental source). At a molecular level, the biologically active analytes can be polypeptide glycoprotein, polysaccharide, lipid, nucleic acid, and a combination thereof.

Of particular interest are biomarkers associated with a particular disease or with a specific disease stage. Such biologically active analytes include but are not limited to those associated with autoimmune diseases, obesity, hypertension, diabetes, neuronal and/or muscular degenerative diseases, cardiac diseases, endocrine disorders, any combinations thereof.

Also of interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are biologically active analytes that are indicative of a microorganism. Exemplary microorganisms include but are not limited to bacterium, virus, fungus and protozoa. Biologically active analytes that can be detected by the subject method also include blood-born pathogens selected from a non-limiting group that consists of *Staphylococcus epidermidis, Escherichia coli,* methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans.*

Biologically active analytes that can be detected by the subject device and methods also encompass a variety of sexually transmitted diseases selected from the following: gonorrhea (*Neisseria gorrhoeae*), syphilis (*Treponema pallidum*), chlamydia (*Chlamydia tracomitis*), nongonococcal urethritis (*Ureaplasma urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional biologically active analytes that can be detected by the subject apparatus and methods encompass a diversity of respiratory pathogens including but not limited to *Pseudomonas aeruginosa,* methicillin-resistant *Staphylococcus aureus* (MSRA), *Klebsiella pneumoniae, Haemophilis influenzae, Staphylococcus aureus, Stenotrophomonas maltophilia, Haemophilus parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsiella oxytoca, Pseudomonas fluorsecens, Neisseria meningitidis, Streptococcus pyogenes, Pneumocystis carinii, Klebsiella pneumoniae, Legionella pneumophila, Mycoplasma pneumoniae,* and *Mycobacterium tuberculosis.*

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alpha-fetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancreas markers include without limitation Amylase, Pancreatitis-Associated protein (PAP-1), and Regenerate in proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx), Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartilage Oligomeric Matrix Protein), Osteocrin, Osteoprotegerin (OPG), RANKL, sRANK, TRAP 5 (TRACP 5), Osteoblast Specific Factor I (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin. DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-suppressor cell antigen, T-cell antigen ratio, T-helper cell antigen, Anti-HCV, Pyrogens, p24 antigen, Muramyl-dipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII:, Antihemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibody markers include those for EGFR, ErbB2, and IGF1R.

Exemplary tyrosine kinase inhibitor markers include without limitation Ab1, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threonine Kinase Inhibitor markers include without limitation AKT, Aurora A/B/B, CDK, CDK (pan), CDK1-2, VEGFR2, PDGFRb, CDK4/6, MEK1-2, mTOR, and PKC-beta.

GPCR target markers include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

For the purposes of this invention, a "therapeutic agent" is intended to include any substances that have therapeutic utility and/or potential. Such substances include but are not limited to biological or chemical compounds such as a simple or complex organic or inorganic molecules, peptides, proteins (e.g. antibodies) or a polynucleotides (e.g. anti-sense). A vast array of compounds can be synthesized, for example, polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters rapidly from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the PD parameters fall outside the desired range during a treatment regime, immediate action may have to be taken as well.

In preferred embodiments physical parameter data is stored in or compared to store profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the scanning sensing system for improved accuracy in determining drug pathways and efficacy in cancer studies.

The term "nucleic acid" when used herein refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "microorganism" when used herein refers to bacteria, actinomycetales, cyanobacteria (unicellular algae), fungi, protozoa, animal cells or plant cells or virus. Examples of microorganisms include but are not limited to pathogens.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins (i.e., antigens), wherein the amino acid residues are linked by covalent peptide bonds. In addition, proteins that contain multiple polypeptide chains that associate through covalent and/or non-covalent interactions are also encompassed by "protein," as used herein.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "individual" when used herein is not limited to a human being, but may also include other organisms including but not limited to mammals, plants, bacteria or cells derived from any of the above.

Aspects of the invention may include one or more of the following advantageous features. Dense and accurate integration of optical manipulating elements can be achieved using planar lightwave circuits technology. Applications for planar lightwave circuits as described herein include new drug discovery and development, disease research, biomarkers discovery, SNP association studies including toxicology and disease susceptibility, and diagnostics including identifying patients predisposed to diseases and identifying patients with particular drug sensitivity.

FIG. 1A illustrates an exemplary scanning sensing system 100 of the invention including a switchable light source 102, a substrate 104, optical sensing sites 112 and a detector 106. The substrate includes excitation waveguides 108 and collection waveguides 110 that cross or intersect at an intersection region 114.

In one embodiment, as shown in FIG. 1A, the switchable light source 102 is coupled to and is in optical communication with one or more of the excitation waveguides 108 at a first edge of the substrate 104. Additionally, the detector 106 is coupled to and in optical communication with one or more of the collection waveguides 110 at a second edge of the substrate 104. Although a single detector at one edge of the substrate is shown, it is envisioned that two or more detectors could be coupled to and in optical communication with one or more collection waveguide at various edges of the substrate (not shown). For example, in one embodiment, where the switchable light source is coupled to a first edge of the substrate, a first detector could be coupled to an adjacent edge and be in optical communication with a first end of a collection waveguide, while a second detector could be coupled to another adjacent edge and be in optical communication with a second end of a collection waveguide. A third detector can be coupled to the edge opposite to the one coupled to the switchable light source and in optical communication with the second end of the excitation waveguides (not shown).

As shown in FIG. 1A, in one embodiment the system 100 can be substantially planar. For example, the switchable light source 102 can be a planar chip. This can be coupled to a planar substrate 104 that is a second chip, that is further coupled to a planar detector 106 that is a third chip. In a particular embodiment, as shown in FIG. 1A, the system 100 is a planar lightwave circuit including three coupled chips. In one embodiment two chips are integrated into a single chip (e.g., an optical switch chip and substrate chip). Such a configuration would be useful in a case where the substrate chip is reusable and can be effectively used for long periods of time. One application of such a configuration would be in a system for detecting biological warfare-associated agents. In such an application it would be advantageous for the system to operate for long periods of time without a need for replacing the chip. In addition, having two chips integrated on a single substrate solves the problem of maintaining the relative alignment of two chips (e.g., a switchable light source chip and substrate chip).

Where the system is used in biological applications, including but not limited to detection of biologically active analytes including nucleic acids, proteins or microorganisms, the substrate can be a multi-element bio-analysis chip.

It is envisioned that crossing or intersecting of the excitation waveguides and the collection waveguides can be a direct physical crossing or intersecting, for example, where the excitation waveguides and the collection waveguides are embedded within the substrate in a single or multiple layers. Alternatively, it is envisioned that the crossing or intersecting involves a physical space or distance between the excitation waveguides and the collection waveguides, for example, where the excitation waveguides and the collection waveguides are embedded within the substrate in separate layers. The optical sensing sites 112 of the system 100 typically are associated with the intersection regions 114. Typically one optical sensing site 112 is associated with each intersection region 114. As illustrated, in one embodiment the number of intersection regions 114 and optical sensing sites 112 is an arrangement of 100 intersection regions 114 and 100 optical sensing sites 112. It is envisioned that the number of intersection regions and optical sensing regions on a substrate chip can be greater than 10, greater than 100, greater than 1,000 or greater than 10,000. It is further envisioned that the density of intersection regions can be greater than 10 per $cm^2$, greater than 100 per $cm^2$, greater than 1,000 per $cm^2$ or greater than 10,000 per $cm^2$. In one embodiment the density of intersection regions is greater than 2,000 per $cm^2$.

As further shown in FIG. 1A, the crossing or intersecting of the excitation waveguides 108 and the collection waveguides 110 can be substantially perpendicular, for example, at an angle of 90°. Alternatively, in certain embodiments the crossing or intersecting can be angled less than or great than 90°.

It is also envisioned that in any of the embodiments described herein, that a first light wave generated by the switchable light source in an excitation waveguide induces the sensor to transduce an optical signal resulting in a second light wave in a collection waveguide, the second light wave being detectable by the detector.

As illustrated in FIG. 1A, in one advantageous embodiment, the system 100 is a planar two-dimensional scanning system. The system 100 in this embodiment includes a planar switchable light source 102, for example, a planar optical switch or an array of switchable lasers, coupled to the plane of the substrate 104, for example, a bio-analysis chip plane. Furthermore, the switchable light source 102 can provide a dynamic source of light for selective and programmed excitation in respect to individual excitation waveguides 108, providing excitation to all of the optical sensing sites 112 along that excitation waveguide 108. A dynamic light source includes but is not limited to a tunable wavelength and/or tunable bandwidth light source. Additionally, the system 100 of this embodiment provides for planar collection of the emitted light from all the excited sensing sites 112 in the collection waveguides 110, specifically in the plane of the substrate 104, such that the light collection is substantially perpendicular to the direction of the light produced in the excitation waveguides 108.

Figure 1B:
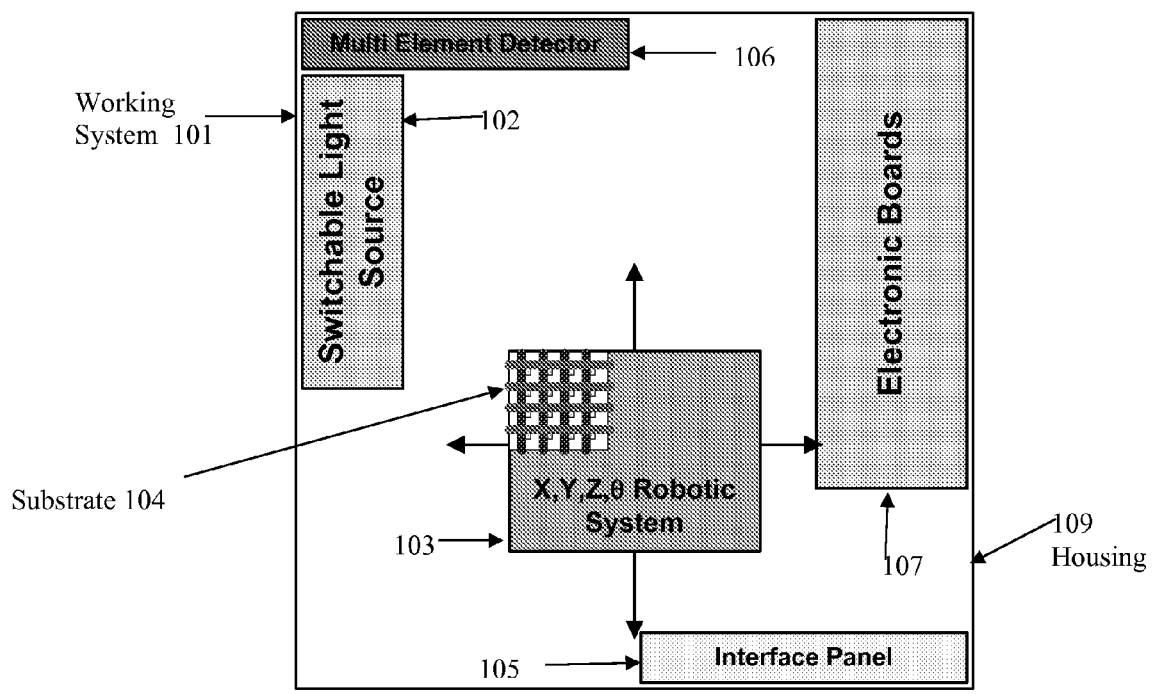
FIG. 1B is block diagram showing the scanning system of the invention as part of a working system in a housing.

FIG. 1B is an exemplary illustration of the scanning system of the invention as part of a working system 101 in a housing 109. While the scanning sensing system illustrated in FIG. 1A is core of the present invention, in order to facilitate the operation of this system, one or more other modules can be included in a working system that includes the scanning sensing system components of the invention.

FIG. 1B illustrates that working system 101 can include housing 109 for enclosing various modules of the working system including but not limited to substrate 104, robotic system 103, switchable light source 102, multi-element detector 106, electronic boards 107 and interface panel 105. Substrate 104, switchable light source 102, and multi-element detector 106, are discussed in detail below.

In regard to housing 109, as shown in FIG. 1B, in one embodiment an enclosure or housing 109 holds in place two fixed chips (e.g., of a 3-chip architecture), namely, switchable light source 102 and multi-element detector 106. Accordingly, in this embodiment substrate 104 chip is movable in relation to switchable light source 102 and multi-element detector 106. Housing 109 can include any number of accurately machined parts and or components and described herein, allowing, for example, the relative alignment of the 3 optical chips. The working system housing can optionally include temperature control and vibration isolation for the working system (not shown).

As shown in FIG. 1B, working system 101 can further include an X, Y, Z, θ robotic system 103 for positioning substrate 104 as required within working system 101. X, Y, Z, θ robotic system 103 can be a translation stage with several degrees of freedom for receiving or accepting substrate 104, holding it in place, and aligning it in relation to the rest of working system 101. As desired, at the end of a run X, Y, Z, θ robotic system 103 can eject substrate 104 from working system 101.

It is envisioned that the working system can further include an aligning system (not shown). An aligning system can include one or more light sources, one or more detectors and one or more cameras for active detection of the position of the substrate of the invention. Based on the detected position, the aligning system can align the substrate to the rest of the working system modules, for example, to provide aligned optical communication between the substrate and the switchable light source.

As shown in FIG. 1B, working system 101 can further include one or more electronic boards 107, for example, an electronic driving board and a control board. It is envisioned that one or more electronic boards can control all the different parts of the working system. Electronic boards 107 can control switchable light source 102 and any other light source present in the system. Electronic boards 107 can be adapted to read any or all of the detectors and cameras in the working system 101. Electronic boards 107 can further be adapted to drive robotic system 103 and control its motion, and optionally monitor and control temperature in different areas of the system. Electronic boards can include logic elements and processors (not shown). It is envisioned that electronic boards can further include embedded software both for controlling the working system and for interfacing the outside world, for example by way of the interface panel 105 having a key-pad or any other input/output port.

As shown in FIG. 1B, working system 101 can additionally include one or more interface panel 105. It is anticipated that the system will have one or more interface panel 105 which allow a user to interface with the system and operate it. Interface panels can include any number of input and output ports for connecting the system to other systems or to an external control console (not shown).

Figure 2A:
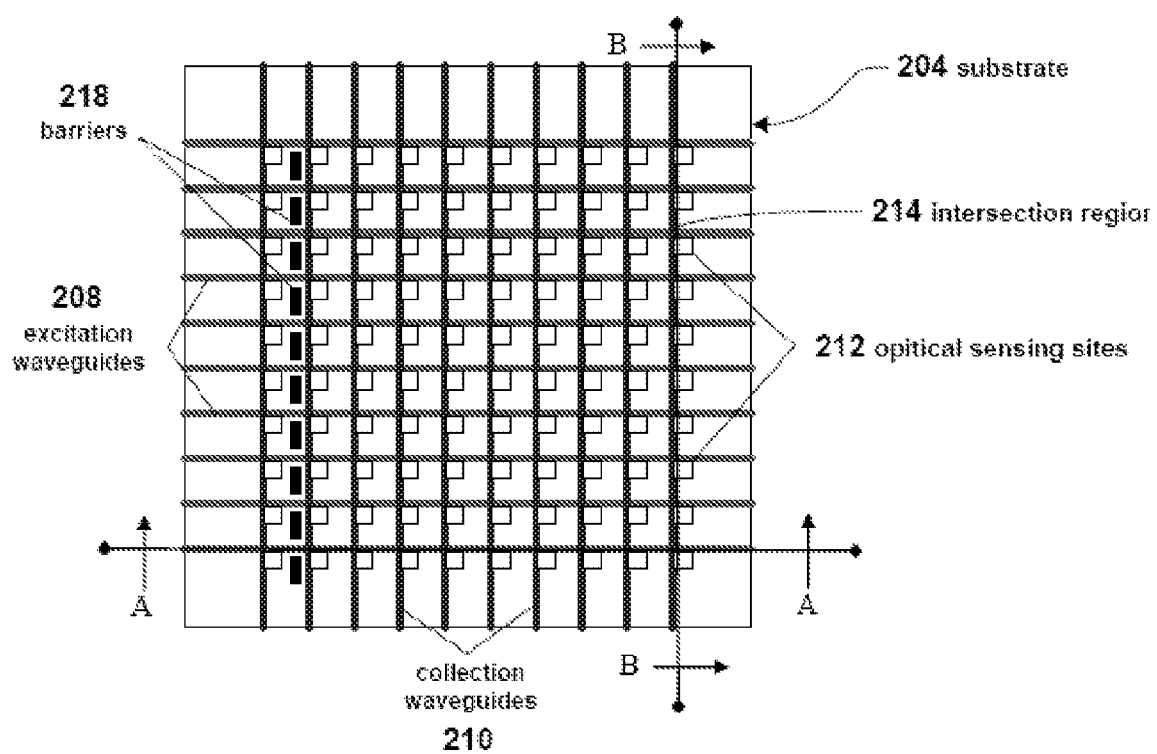
FIG. 2A is a schematic of the substrate of the invention including excitation and collection optical waveguides in conjunction with optical sensing sites and barriers.

FIG. 2A illustrates an exemplary substrate 204 of the system of the invention further including barriers 218 intended to block stray light within the substrate and reduce crosstalk between the different elements of the substrate. The barriers 218 can be light absorbing or light reflecting. The barriers 218 can be variously sized, shaped and positioned between the collection waveguides 210 and/or the excitation waveguides 208 in any of a number of orientations to achieve a desired optical effect. As shown in FIG. 2A, the barriers 218 can be arranged in a row between two adjacent collection waveguides and proximal to the optical sensing sites 212 and intersection region 214.

Figure 2B:
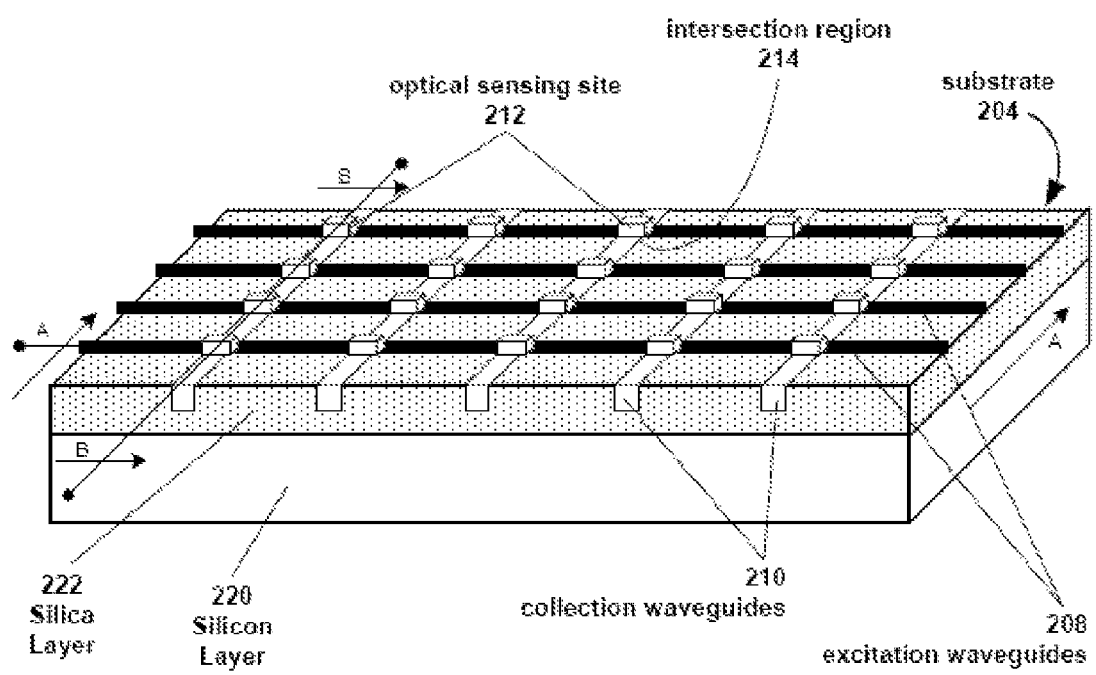
FIG. 2B is a perspective view of the substrate including excitation and collection optical waveguides in conjunction with optical sensing sites.

As shown in FIG. 2B, (in this view a top cladding layer is not shown) in one embodiment the substrate 204 can include excitation waveguides 208 and collection waveguides 210 embedded beneath a surface of the substrate 204 in multiple layers. As shown, the excitation waveguides 208 cross, physically intersect, and are in optical communication with the collection waveguides 210 at the intersection regions 214. In the embodiment shown in FIG. 2B, the optical sensing site 212 is positioned at the intersection region 214 above and in optical communication with the excitation waveguides 208. As further shown in FIG. 2B, the substrate 204 includes multiple layers including a Silicon layer 220 and a Silica (SiO2) layer 222, wherein the collection waveguides 210 are embedded within the Silica (SiO2) layer 222.

Figure 2C:
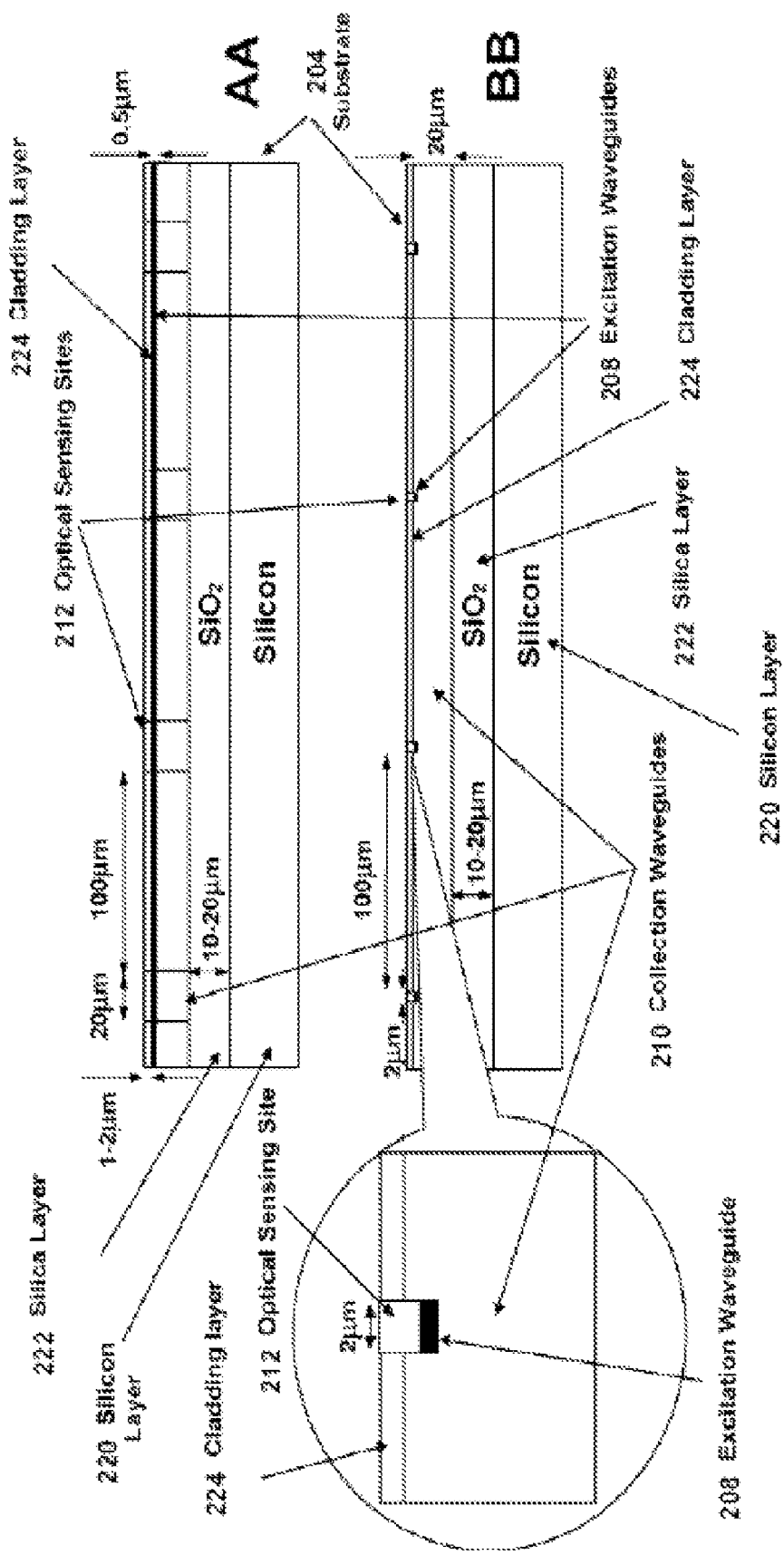
FIG. 2C is a schematic of two cross-sectional views (AA and BB) of the substrate shown in FIGS. 2A and 2B.

As shown in FIG. 2C, in another embodiment the substrate can include excitation waveguides 208 and collection waveguides 210 embedded underneath a surface of the substrate 204 in a single layer. As shown, the excitation waveguides 208 cross, physically intersect and are in optical communication with the collection waveguides 210. In contrast to the embodiment shown in FIG. 2B, here the intersection between excitation waveguides 208 and collection waveguides 210 occurs internal to the collection waveguides 210. As further shown in FIG. 2C, the substrate 204 includes multiple layers including a Silicon layer 220, a Silica (SiO2) layer 222, and a cladding layer 224. As shown, the excitation waveguides 208 and collection waveguides 210 can be embedded within the Silica (SiO2) layer 222. Additionally, the optical sensing site 212 can be embedded within both the cladding layer 224 and the Silica (SiO2) layer 222. Optionally, the optical sensing site can be embedded solely within the cladding layer (not shown).

It is envisioned that the excitation waveguides and collection wave guides can be single-mode or multi-mode waveguides. In one embodiment, the excitation waveguides are single-mode and the collection waveguides are multi-mode. It is envisioned that waveguide configurations can include single- or multi-mode configurations in either vertical or lateral orientations within a waveguide. For example, in one specific and non-limiting embodiment, the excitation waveguides 208 can support a single mode in the vertical dimension and multi modes in the lateral dimension. Optionally, as shown in FIG. 2A, the excitation waveguides 208 and the collection waveguides 210 can span the entire substrate from one edge to another edge.

As shown in FIG. 2C, the substrate 204 components and optical sensing sites 212 can include dimensions. FIG. 2C shows two cross-section views of the substrate 204. View AA is a cross-section view in plane A as indicated in FIG. 2A and FIG. 2B. View BB is a cross-section view in plan B as indicated in FIG. 2A and FIG. 2B. As shown in FIG. 2C, the thickness of the cladding layer 224 above the excitation waveguides can be about 0.1 µm to 20 µm. In one embodiment the cladding layer 224 thickness is about 1-2 µm. By way of a non-limiting example, as shown in FIG. 2C, an opening of the optical sensing site 212 can include the following dimensions: about 20 µm×2 µm. The distance between collection waveguides 210 can range from about 1 µm to 1000 µm. For example, as shown in FIG. 2C, the distance between collection waveguides 210 can be about 100 µm. The distance between collection waveguides 210 and the Silicon layer 220 can be about 1 µm to 100 µm. For example, as shown in FIG. 2C, the distance between collection waveguides 210 and the silicon layer 220 can be about 10-20 µm.

As shown in FIGS. 2B and 2C, the excitation waveguides 208 and collection waveguides 210 can be channel waveguides. Exemplary ranges for waveguide dimensions in the embodiment shown in FIGS. 2B and 2C include about 0.2 to 100 µm thick and about 1 to 100 µm wide. By way of non-limiting example only, the excitation waveguides 208 can include cross-section dimensions of about 0.5 µm×2 µm and the collection waveguides 210 can include cross-section dimensions of about 20 µm×20 µm.

Figure 2D:
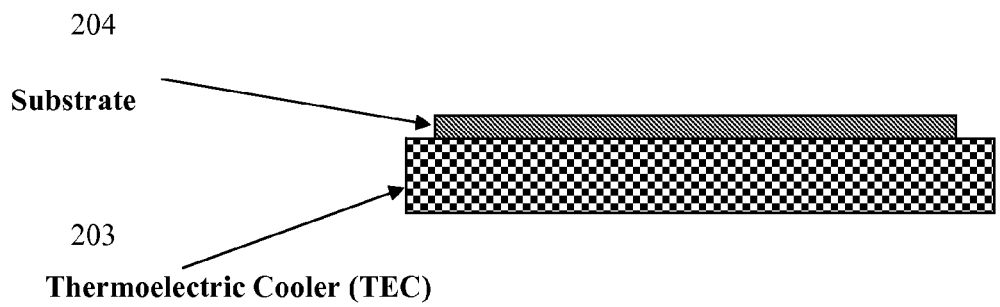
FIG. 2D is a schematic of a side view of the substrate in relation to a thermoelectric cooler.

FIG. 2D in a side view illustrates another embodiment of substrate 204 of the invention in relation to a thermal transfer element 203, for example, a thermoelectric cooler (TEC). Thermal transfer element 203 is a temperature control system useful for heating or cooling a chip, for example, substrate 204. Although the thermal transfer element may be referred to herein as a cooling element, it is to be understood that where the thermal transfer element is configured to increase and decrease the temperature of a chip, the component functions essentially as a heating and as a cooling element depending on the induced direction of the electrical current. The thermal transfer element can provide a range of useful temperatures. For example, the thermal transfer element can be configured to provide a temperature in the range between about −40° C. to about 120° C. as desired. The thermal transfer 203 element can be adapted to receive substrate 204 of the invention. The thermal transfer element 203 can be adapted to contact part or all of a surface of the substrate 204 of the invention.

Providing thermal transfer element 203 in conjunction with substrate 204 of the invention is useful, for example, for the amplification of tested sample molecules through processes such as Polymerase Chain Reaction (PCR) as described herein. In use, the embodiment as described for FIG. 2D provides the capability of controlling the temperature of the entire substrate such that as the temperature of the entire substrate is cycled, samples at any optical sensing site can be amplified by PCR simultaneously.

Figure 2E:
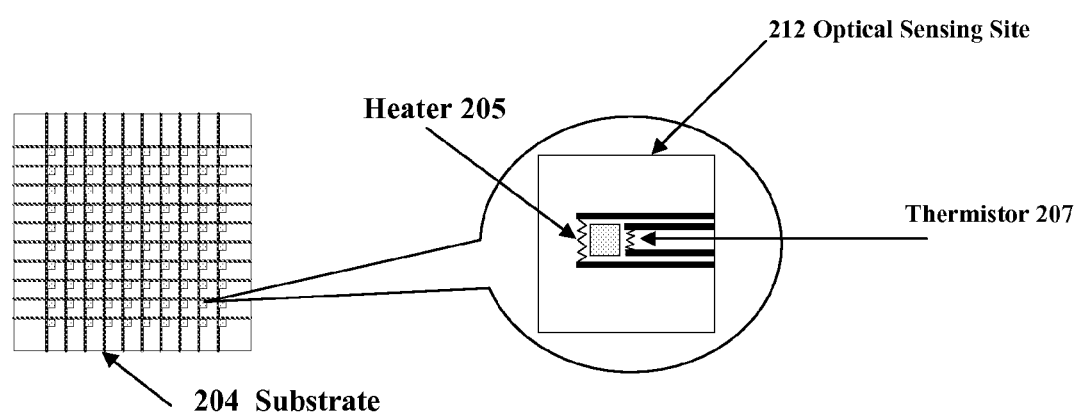
FIG. 2E is a schematic of the substrate of the invention illustrating details of an optical sensing site including a heater and a thermistor.

FIG. 2E illustrates another embodiment of substrate 204 of the invention wherein optical sensing site 212 includes heater 205 and thermistor 207. In this embodiment, optical sensing site 212 of substrate 204 can include heater 205, for example, a thin-film heater, in the vicinity of each sensing sites 212. Heater 205 can be adapted to enable individual temperature control for each sensing site 212. In addition to heater 205, thermistor 207 can be located at or near each sensing site 212 thereby providing for measuring the local temperature. In use, this embodiment provides the capability of running the same or any desired different number of cycles and the same or any desired different temperature profiles for each and every sensing site.

Advantageously, the embodiments described for FIGS. 2D and 2E can support real-time PCR. As described herein, since optical detection is done from within the substrate, signal detection in both embodiments (see FIGS. 2D and 2E) can be done while the samples are in the process of the amplification cycles, thereby enabling real time analysis of the PCR process.

Figure 2F:
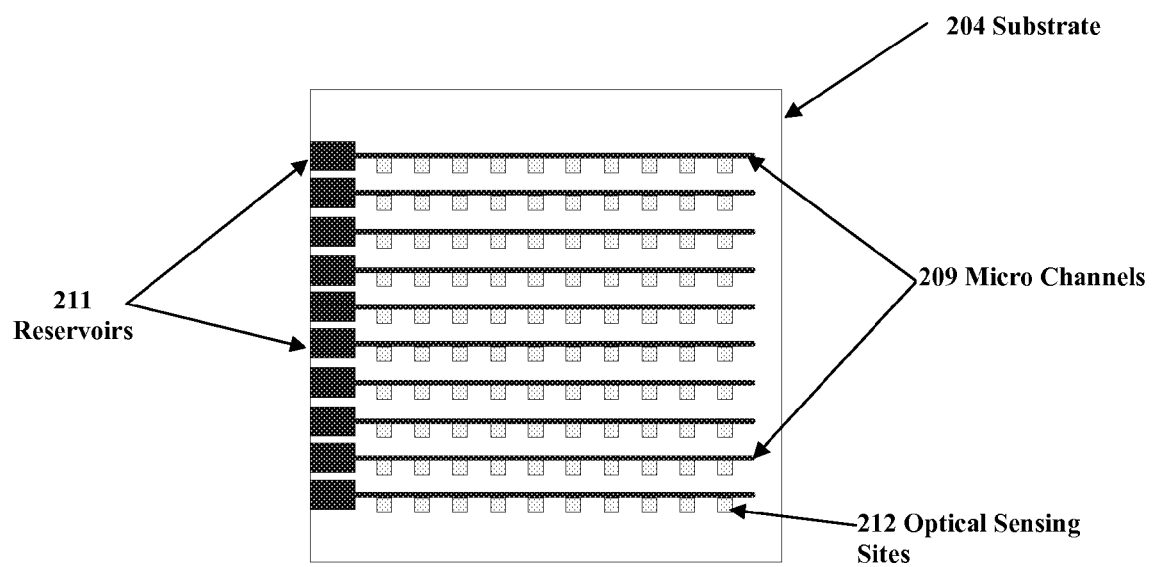
FIG. 2F is a schematic of the substrate of the invention including reservoirs and micro channels in relation to optical sensing sites.

FIG. 2F illustrates yet another embodiment of substrate 204 of the invention wherein substrate 204 additionally includes reservoirs 211 and microchannels 209 in relation to optical sensing sites 212. As such, in this embodiment microfluidics are incorporated into the substrate. Microfluidics can be adapted to drive liquid (in this case the tested sample) using the capillary effect across the substrate. As illustrated in FIG. 2F, this can be achieved by an arrangement of microchannels 209, optionally of varying width, which force the sample from one or more reservoirs 211 to optical sensing sites 212 which can include etched wells to receive the sample. The microchannels can be either etched on the face of the chip itself or can be added as an external structure on a surface of the sensing chip.

In use, it is envisioned that a sample to be tested can be pipetted into a reservoir at one end of the substrate. The sample can then be distributed using the microfluidic system to the optical sensing sites and sensing wells where it is allowed to bind to pre-spotted probes and can subsequently be optically scanned and analyzed. Several reservoirs may be used to separate different samples/patients or for running several parallel tests.

Figure 3A:
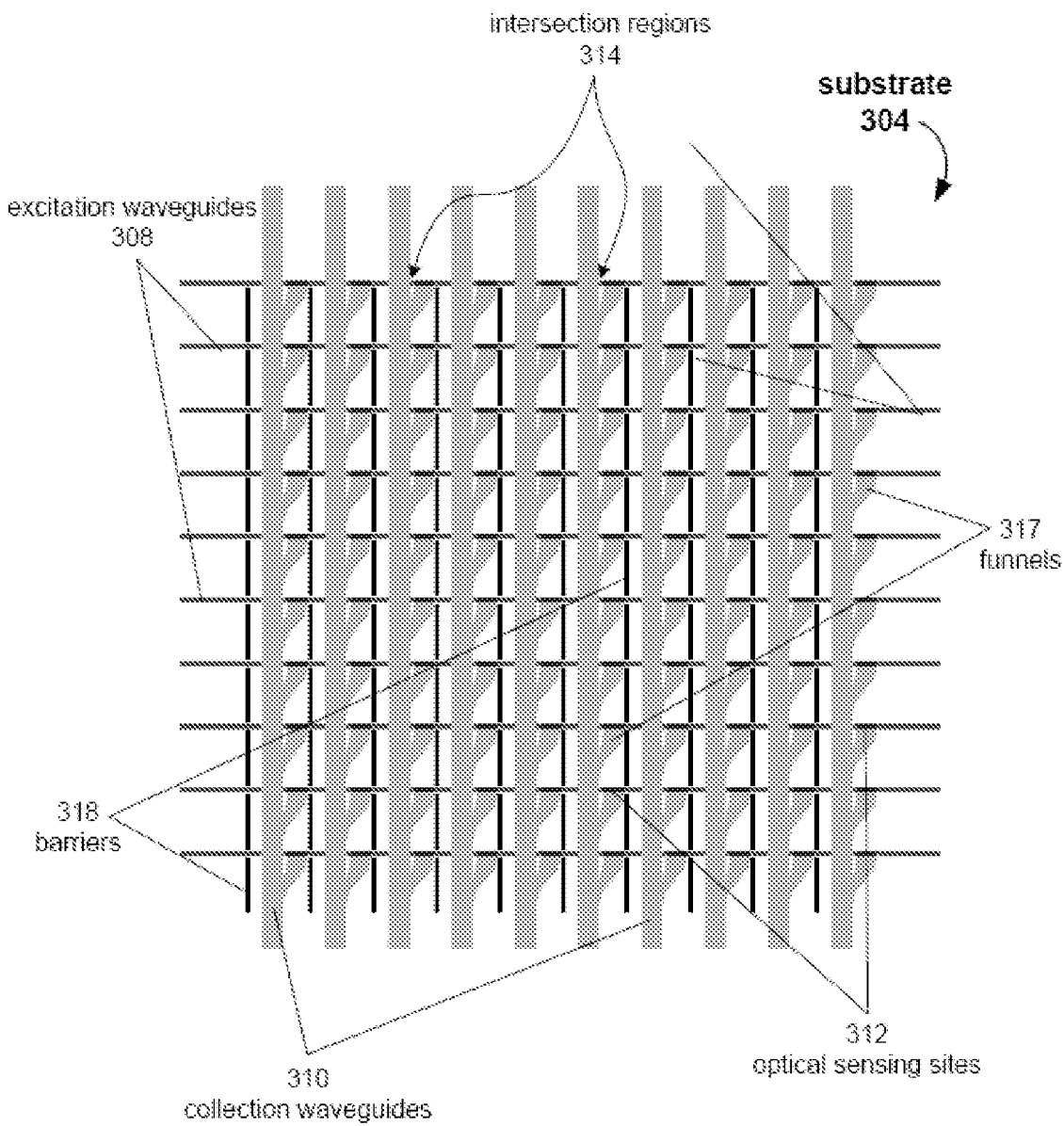
FIG. 3A is a schematic of the substrate of the invention including excitation and collection optical waveguides in conjunction with optical sensing sites, barriers and funnels.

FIG. 3A in a top view illustrates an exemplary substrate 304 of the system of the invention wherein the collection waveguides 310 include funnels 317 (shown in detail in FIG. 3B) for collecting light.

As shown in the example in FIG. 3A, the substrate 304 can include a 10×10 array consisting of 10 excitation waveguides 308 (e.g., 5 µm wide×2 µm deep), 10 collection waveguides 110 (e.g., 30 µm wide×10 µm deep), 100 optical sensing sites 312 (e.g., wells 30 µm long×5 µm wide×10 µm deep), 100 funnels 317 for collecting light from the optical sensing sites 312 and barriers 318 (e.g., light absorbing channels) to reduce crosstalk between the optical sensing sites 312. Although the example shown in FIG. 3A includes a 10×10 array of excitation waveguides 308 and collection waveguides 110, it is envisioned that the substrate can include greater than 10, greater than 100 or greater than 1,000 excitation waveguides 308 and collection waveguides 110.

In the embodiment shown in FIG. 3A, excitation light can be coupled into one or more excitation waveguides 308 on the left hand side of the substrate 304 through, for example, chip-to-chip butt coupling. Excitation light can travel along the excitation waveguides 308 and couple into the optical sensing sites (e.g., wells) through an evanescent field tail. Additionally, the switchable light source can include one or more waveguide and can be evanescently coupled to the substrate through a proximate arrangement of the one or more switchable light source waveguide and one or more excitation waveguide of the substrate. Excited fluorescence generated in the optical sensing site 312 can be collected along the long facet of the optical sensing site 312 into the funnels 317. The funnels 317 can channel the light into the collection waveguides 310. The light in the collection waveguides 310 can be coupled out at the "bottom" of the substrate 304 into a detector array (not shown). Light scattered outside the optical sensing sites 312 can be blocked by a series of barriers 318 (e.g., light absorbers) to avoid crosstalk between parallel collection waveguides 310.

In one embodiment, the substrate shown in FIG. 3A includes two waveguide layers. As illustrated in cross-sectional view in FIG. 3C, a first 2 µm thick bottom layer can include the excitation waveguide 308. The bottom layer can have a higher refractive index in order to increase the evanescent field tail presence in the optical sensing sites. An upper 10 µm thick layer can contain the optical sensing site and the light collection structures (funnels and waveguides). The upper layer can have a lower refractive index than the bottom layer in order to minimize light loss when coupling the light out of the substrate to the detector.

In a particular embodiment of the above, both the excitation and collection waveguides are multimode. Furthermore, the switchable light source (e.g., an optical switch or an array of light generators coupled to an array of waveguides) can include single-mode waveguides, that can be butt-coupled or can evanescently couple to the substrate.

Figure 3B:
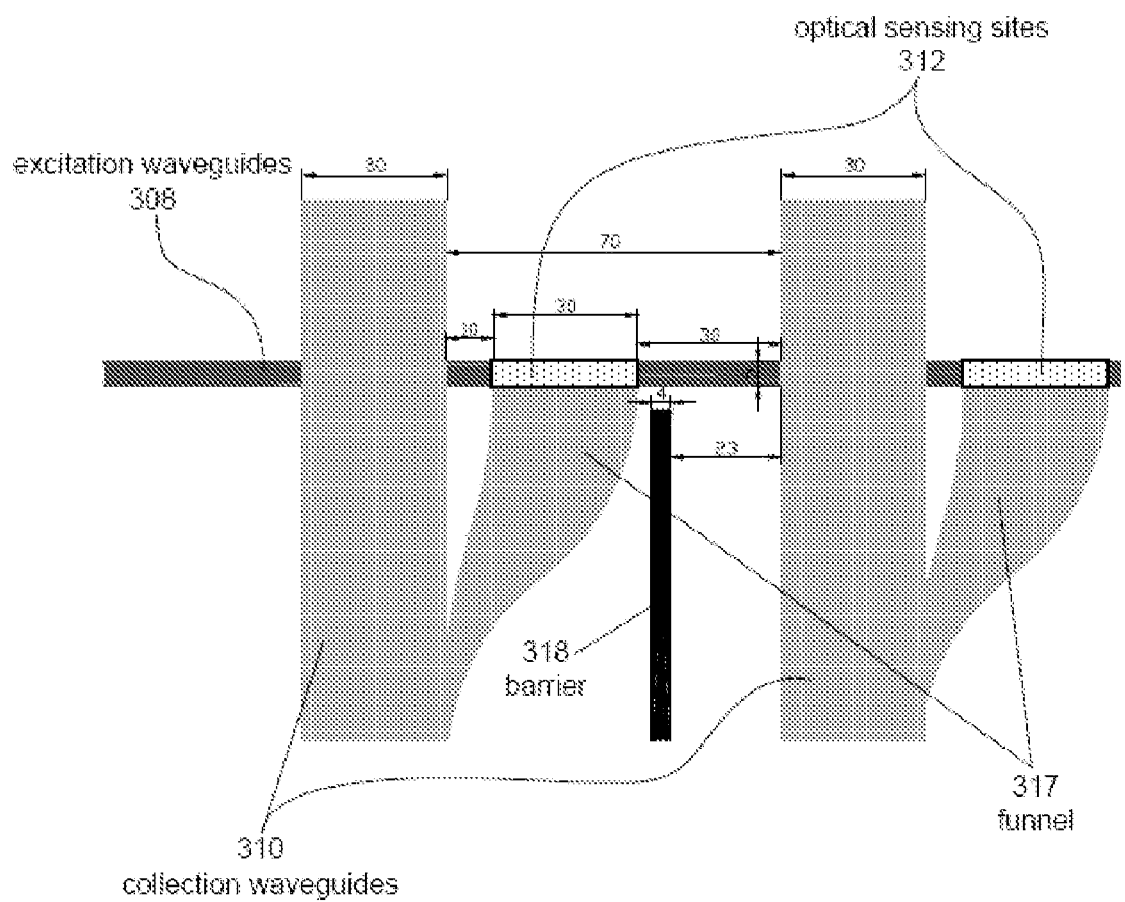
FIG. 3B is a schematic showing and enlarged view of substrate features shown in FIG. 3A.
Figure 3C:
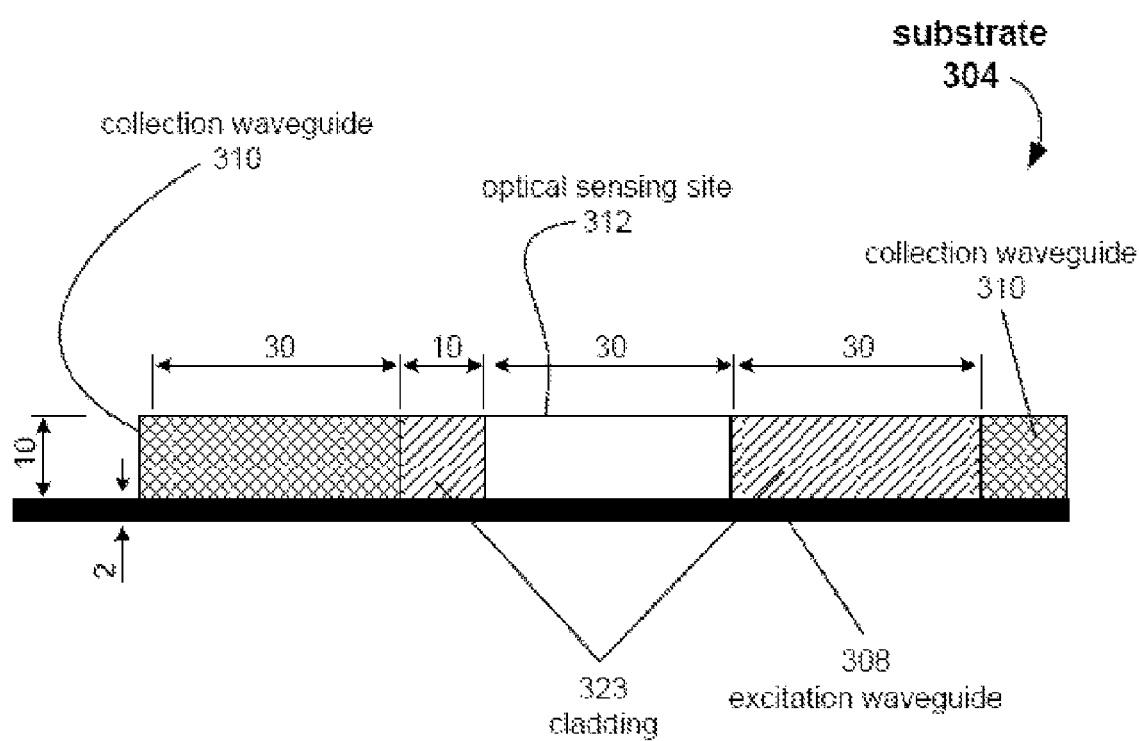
FIG. 3C is a schematic of a cross-sectional view of the substrate shown in FIG. 3B.

As shown in cross-sectional view in FIG. 3C, in order to minimize the loss of light at the waveguide crossing points due to light coupling from the collection waveguides 310 into the excitation waveguides 308, the excitation waveguides 308 can be thinner than the collection waveguides 310. For example, as shown in FIGS. 3B and 3C, the excitation waveguides 308 can have a width of 5 µm (see FIG. 3B) and a height of 2 µm (see FIG. 3C). As further shown, the collection waveguides 310 can have a width of 30 µm (see FIGS. 3A and 3B) and a height of 10 µm (see FIG. 3C).

It is envisioned that light coupled at the waveguides crossing points between the excitation waveguides and the collection waveguides can shine directly into the optical sensing sites, thereby increasing light excitation rather than being lost.

As shown in FIG. 3B, the optical sensing sites can be wells that are narrow (5 µm) and long (30 µm) with light collectable along the long facet. Such a configuration increases the efficiency of light collection. In addition, light excitation coupling into the well can increases due to the long coupling length. The well dimensions (5×30×10 µm$^3$) yield a volume of 1.5 pico-liter. Larger wells are also envisioned in a variety of sizes yielding volumes ranging from about 0.1 pico-liter to 100 micro-liter.

The funnel can have a radii for the collection, confinement and coupling of light into the collection waveguides. Suitable ranges for radii can include from about 100 µm to about 1000 µm.

The barriers 318 as illustrated in FIGS. 3A and 3B, can be trenches filled with light absorbing material (e.g., a metal such as gold). Where the barriers 318 are trenches, the trenches can include openings above the excitation waveguide 308 to avoid loss at the crossing points (not shown).

The overall dimensions of the substrate illustrated in FIG. 3A can be 1.2×1.2 mm$^2$. Margins can optionally be included around the substrate to adjust the overall dimensions as desired.

Figure 4A:
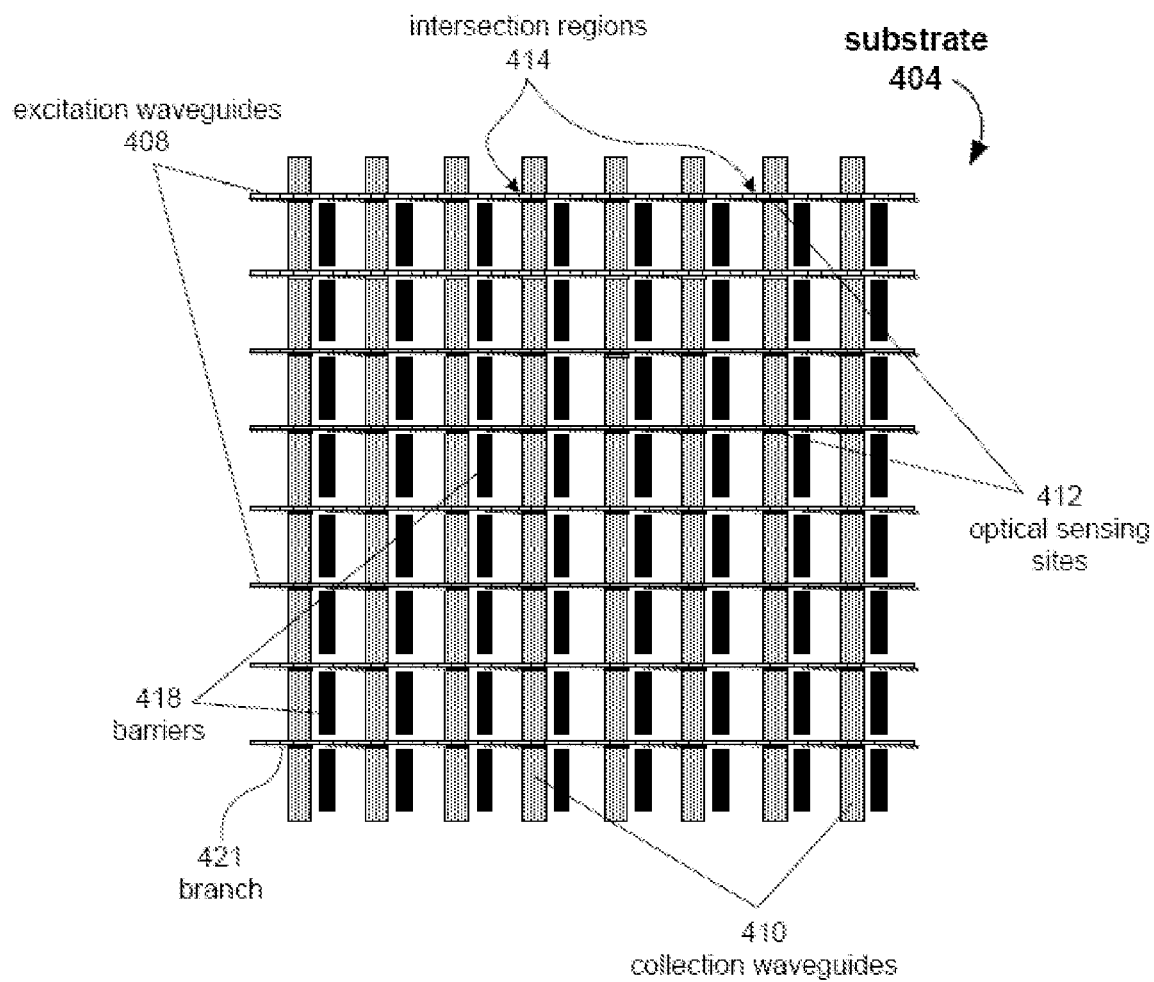
FIG. 4A is a schematic of the substrate of the invention including excitation and collection optical waveguides in conjunction with optical sensing sites, barriers and branches.

FIG. 4A illustrates an exemplary substrate 404 of the system of the invention wherein the Excitation waveguides 408 include a plurality of branches 421 (shown in detail in FIG. 4B) for tapping light from the excitation waveguides and coupling it into the sensing wells.

Figure 4B:
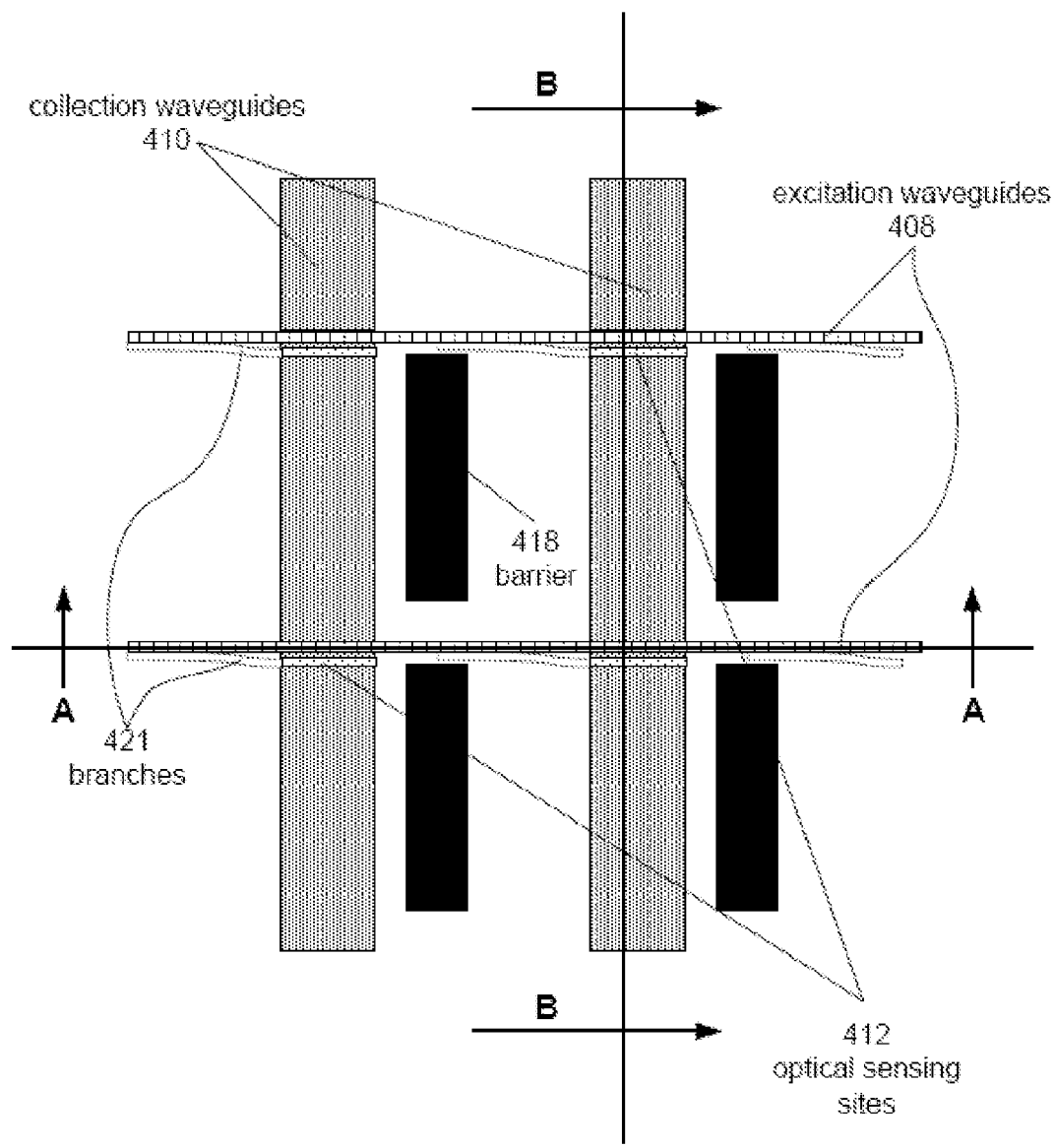
FIG. 4B is a schematic showing and enlarged view of substrate features shown in FIG. 4A.
Figure 4C:
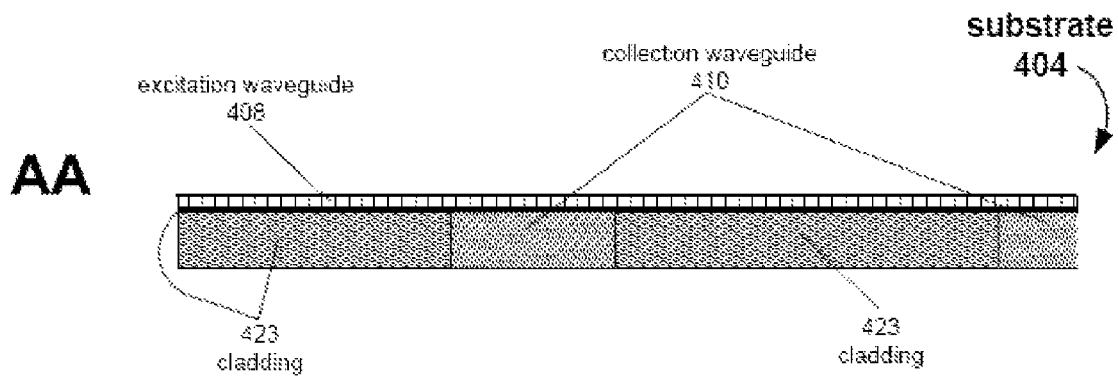
FIG. 4C is a schematic of a cross-sectional view in a plane (AA) of the substrate shown in FIG. 4B.
Figure 4D:
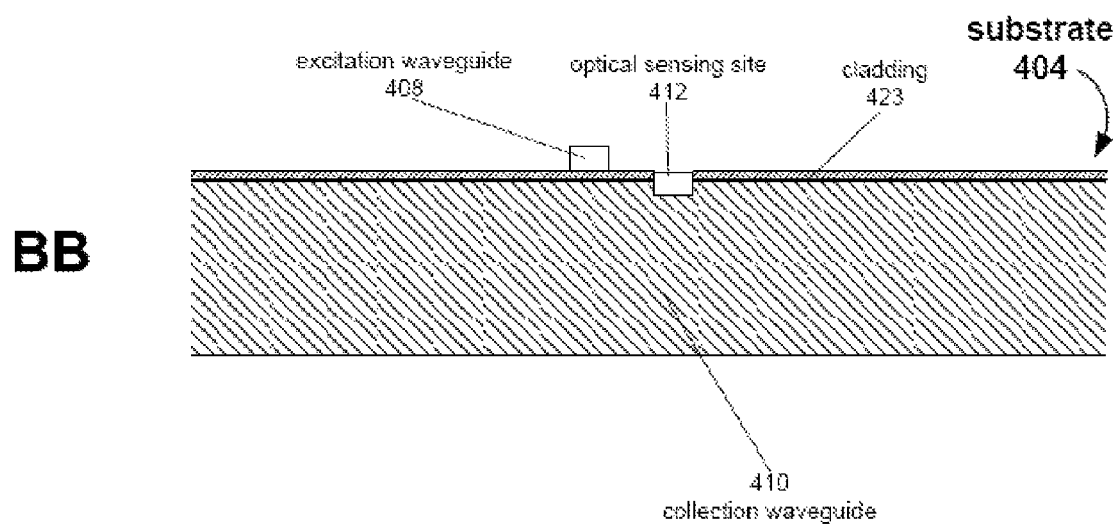
FIG. 4D is a schematic of a cross-sectional view in a plane (BB) of the substrate shown in FIG. 4B.

In the embodiment shown in FIG. 4A, the substrate 404 can be made up of several waveguide layers (e.g., three waveguide layers). Such a configuration can be useful, for example, to optimize excitation and fluorescence collection while minimizing loss and crosstalk. FIGS. 4C and 4D are schematic cross-section views of the substrate 404 through planes at (AA) and (BB) respectively as indicated in FIG. 4B.

In one embodiment the substrate consists of three waveguide layers having core refractive index of 1.7 and clad reflective index of 1.4. Useful core refractive index values range from about 1.45 to 1.7, and useful clad refractive index values range from about 1.4 to 1.44.

As shown in FIGS. 4C and 4D, in one embodiment where the substrate 404 includes three waveguide layers, a first bottom layer can be about 10 µm thick and include the collection waveguides 410. In the embodiment illustrated in FIG. 4A, the collection waveguides 410 can be 30 µm wide, multimode and traverse the substrate 410 from substantially edge to edge. A second middle waveguide layer can be 0.5 µm to 1 µm thick and include coupling waveguide branches 421 (see FIGS. 4A and 4B). The branches 421 can couple excited light into the optical sensing sites, which can be wells. A third top layer can be 2 µm thick and include single-mode excitation waveguides 408 and traverse the substrate substantially from edge to edge.

The substrate of the scanning sensing system can made up of any of a number of well known materials suitable for use in planar light circuits. For example, useful substrate materials include but are not limited to Silica (SiO2), glass, epoxy, lithium niobate and indium phosphide as well as combinations thereof. The waveguides disclosed herein can be made up of Silicon, Silica (SiO2) and derivatives thereof, silicon oxynitride (SiON) and derivatives thereof, silicon nitride (SiN) and derivatives thereof, polymers, lithium niobate and indium phosphide as well as combinations thereof. In one embodiment, UV light is used to change the refractive index of a waveguide material after deposition.

Figure 5:
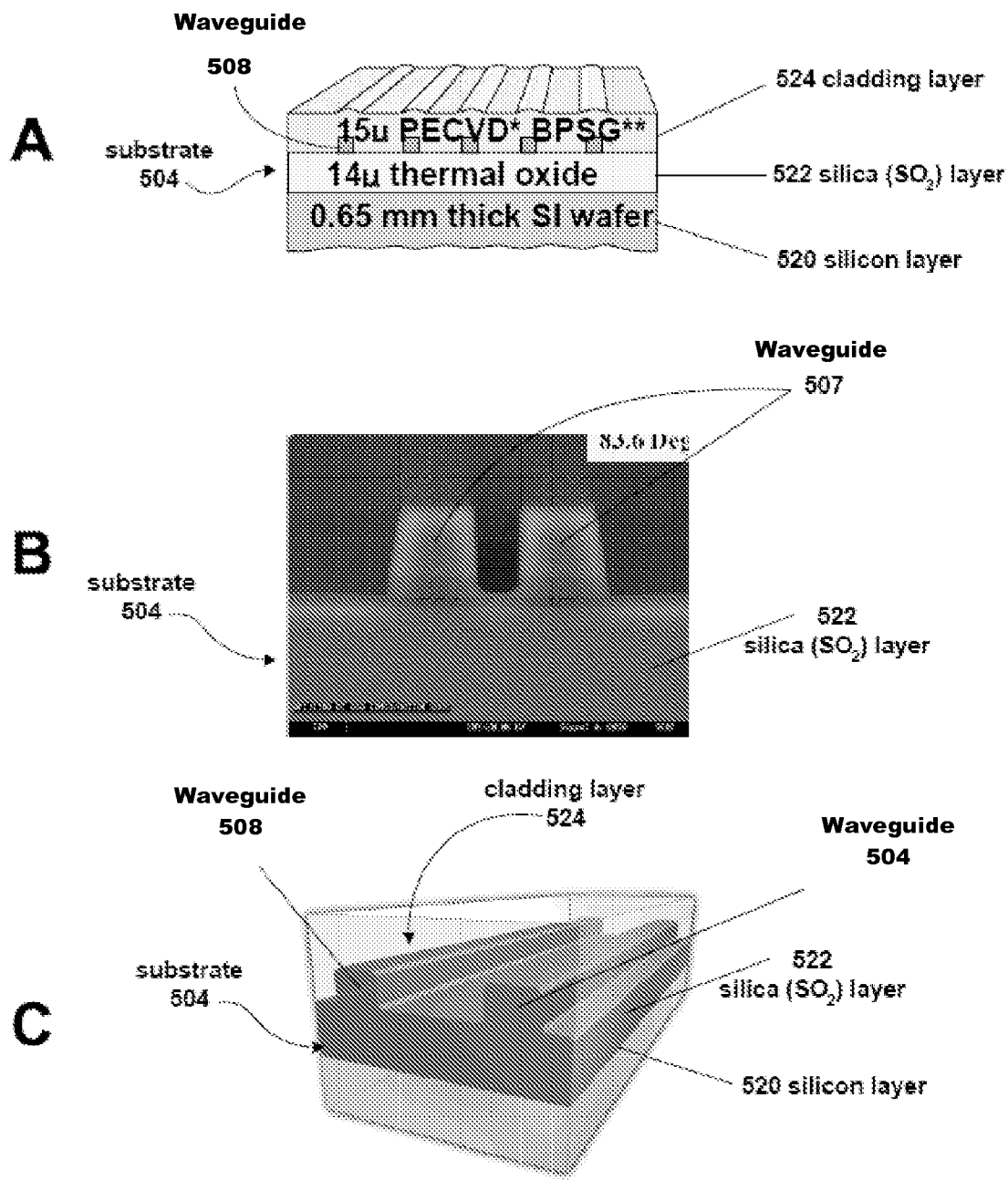
FIG. 5A is a schematic of a general substrate including typical layers and waveguides representative of those of the current invention.
FIG. 5B is a photomicrograph image of waveguides representative of those of the invention and a silica layer.
FIG. 5C is a perspective view of waveguides and associated layers.

FIG. 5A illustrates an exemplary silicon layer 520 of the substrate 504. For example, the silicon layer 520 can be made up of a silicon wafer having a thickness from about 0.1 mm to 10 mm. In another example the silicon wafer can have a thickness from about 0.3 to 1 mm. In a particular example as illustrated in FIG. 5A, the silicon wafer has a thickness of 0.65 mm. As shown in FIG. 5A in one embodiment, the silica (SiO2) layer 522 is a 14 µm thermal oxide layer of Silica (SiO2) created by placing the Silicon in an oxygen-rich environment inside a furnace at high temperature. The top Silicon layer oxidizes over time (several hours) creating a SiO2 layer. Additionally, as shown in FIG. 5A, in one embodiment, the cladding layer 524 is 15 µm thick and deposited by a PECVD (Plasma-Enhanced Chemical Vapor Deposition) process after etching to produce the waveguides 508.

It is envisioned that the various layers of the substrate can include different refraction index properties. For example, a wafer layer of silicon has a higher refraction index than a cladding layer of silica deposited thereon.

As shown in FIG. 5B (illustrated with a photomicrograph prior to deposition of a cladding layer), in some embodiments, the substrate 504 can include two waveguides 507 arranged for light wave coupling on a silica (SiO2) layer 522. Alternatively, as shown in FIG. 5C, two waveguides 508 can be arranged for guiding uncoupled light waves on a silica (SiO2) layer 522 and overclad with a cladding layer 524.

The optical sensing sites in one embodiment are in the form of wells, for example, etched wells (see FIG. 4D expanded view). Where the optical sensing site is a well, it can act as a vessel for a liquid sample. In another embodiment the optical sensing sites are a region on the surface of the substrate, for example, above the intersection region of the excitation waveguides and the collection waveguides (not shown). In a further embodiment, the optical sensing sites are biochemical interaction sites. For example, where the optical sensing site is a well containing a sensor single stranded DNA oligonucleotide having a fluorescent tag attached, a solution containing a target complementary single stranded DNA added to the well could biochemically interact by base-pairing with the sensor within the optical sensing site (not shown). In another example the optical sensing site is a location or well containing one or more immunoassay reagent for conducting an immunoassay as described herein.

In a particular embodiment, the optical sensing sites comprise optical transducers (not shown). An optical transducer is defined as any device that generates a measurable change (wavelength, amplitude or phase) to the incoming first light wave and can thus be monitored in the outgoing second light wave. In one embodiment the optical transducers are fluorescence wells including fluorescent or luminescent compounds, wherein light waves guided by the excitation waveguides excite the fluorescent or luminescent compound in the wells in the presence of a target, and the collection waveguides collect and guide light emitted from the wells to the detector, for example at the edge of the chip (not shown).

The sensor of the optical sensing site of the system can be a sensor that discriminates or interacts with a target (e.g., a biologically active analyte) in a sample from, for example, a biological, man-made or environmental source. As discussed above, a first lightwave can induce the sensor to transduce an optical signal to a second light wave. In one embodiment where the sensor is capable of discriminating or interacting with a target in a sample, a measurable change in the second light wave can result when the sensor discriminates or interacts with the target. Upon detection of the change in the second light wave using the detector of the system, presence of the target in the sample is known.

Any of a number of sensors can be used with the scanning sensing system to measure phenomenon associated with sensing of a target in a sample. Examples of suitable sensors include, but are not limited to, a fluorescence well or cell, an absorption cell, an interferometric sensor, a diffractive sensor or a surface plasmon resonance (SPR) detector. For a fluorescence well or cell, the phenomenon measurable can be light emission from luminescent or fluorescent molecular tags. For example, emitted light at an altered wavelength can be measured. In the case of an absorption cell, changes in the sample optical density (OD) can measurably affect the intensity of the light passing through the sample. For an interferometric sensor, changes in the effective refractive index of a waveguide generate a phase different between two beams of light leading to different interference patterns measurable as a difference in intensity at the detector. For a diffractive sensor, changes in the effective refractive index at the surface of a diffractive element, for example, a grating, affect the diffraction angle of the light for a given wavelength or alternatively affect the wavelength at a given diffraction angle. In the case of a SPR sensor, changes in the effective refractive index at a metal-dielectric interface affect the resonance conditions for generating surface plasmons.

Figure 6A:
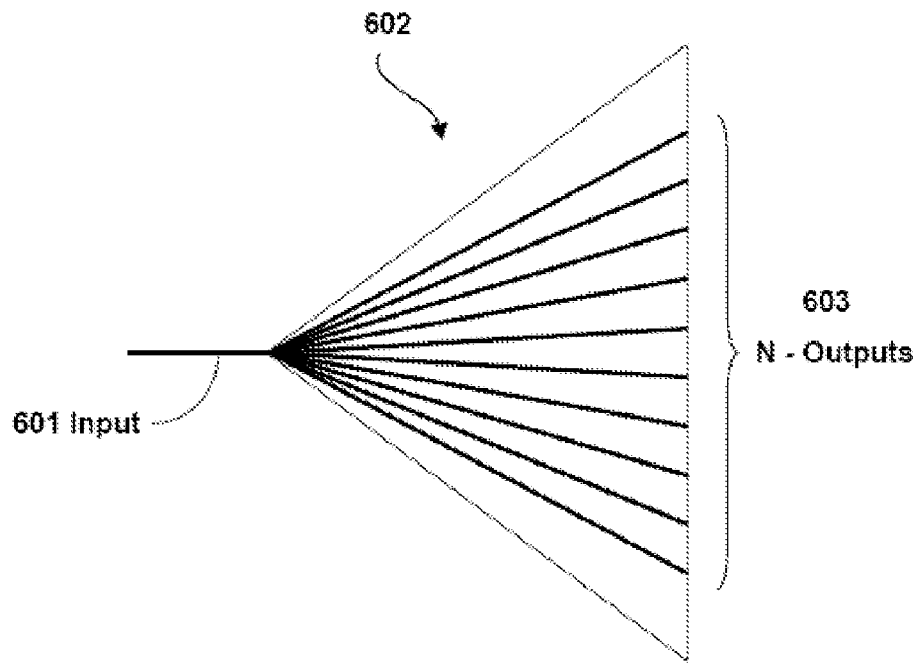
FIG. 6A is a schematic of the switchable light source of the invention including inputs and outputs.
Figure 6B:
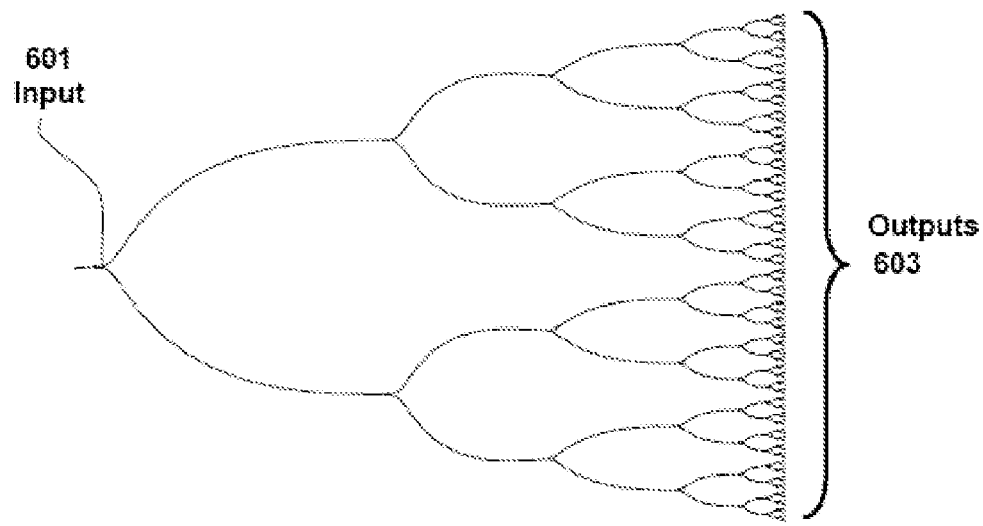
FIG. 6B is a schematic of a branched architecture between the inputs and outputs of the switchable light source.

FIG. 6A illustrates an exemplary switchable light source 602 of the system of the invention, including one or more inputs 601 as a primary source of light for coupling to a light generator The light generator can be any source of electromagnetic radiation emitting one or more discrete spectral-lines or a continuous spectrum (not shown). In one preferred embodiment the light generator is a laser source emitting in one or more well defined wavelengths. In a second preferred embodiment the light generator is a tunable laser that can be tuned to emit light in one wavelength within a predefined range. As illustrated, switchable light source 602 further includes a plurality of outputs 603 shown in FIG. 6A as N—Outputs. The number of outputs 603 included in switchable light source 602 can be variable based on the intended use. For example, in certain applications the number of outputs 603 can be greater than 10 outputs. In one embodiment the number of outputs 603 can be great than 100 outputs. In a further embodiment the number of outputs 603 can be greater than 1,000 outputs. In another embodiment the number of outputs 603 ranges from about 50 to 500. In a particular embodiment, the number of outputs 603 is about 128. As shown in FIG. 6A, in one embodiment, the switchable light source includes outputs 603 that fan out from an input 601. As illustrated in FIG. 6B, in one embodiment a branched architecture stemming from the input 601 to the outputs 603 can be used. Although only one input is shown in FIGS. 6A and 6B, it is envisioned that multiple inputs 601 can be used.

Figure 6C:
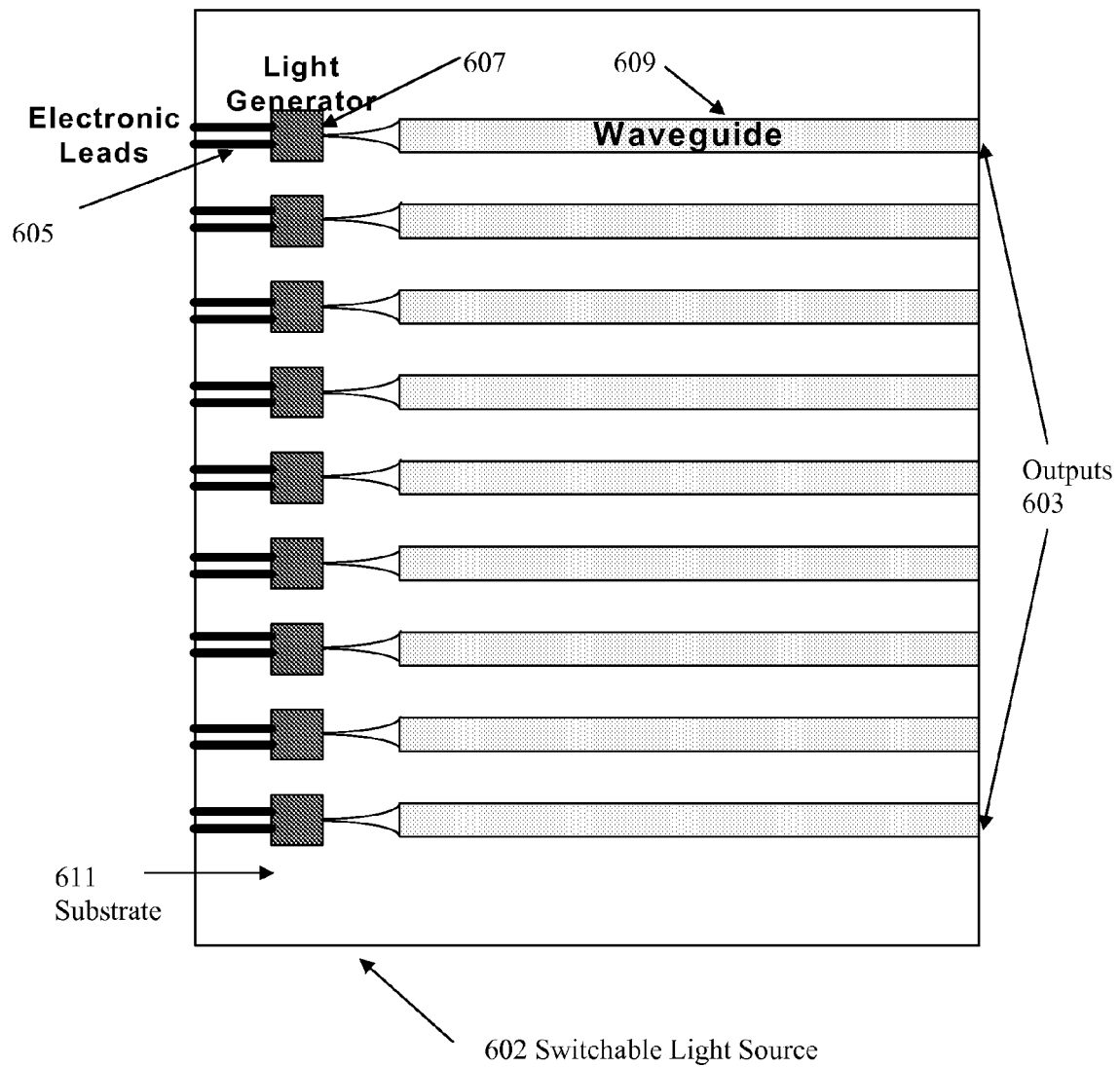
FIG. 6C is a schematic of another embodiment of the switchable light source of the invention including light generators and waveguides.

FIG. 6C illustrates another exemplary switchable light source 602 of the system of the invention including multiple outputs. In this embodiment switchable light source 602 includes a plurality of waveguides 609, light generators 607 and electronic leads 605. As shown in FIG. 6C waveguides 603 can be arranged in parallel across substrate 611. In other embodiments waveguides are arranged in a non-parallel fashion (not shown). Waveguides 609 can terminate in outputs 603 as described herein.

As shown in FIG. 6C, light generators 607 as described herein can be arranged in optical communication with waveguides 609. As further shown in FIG. 6C, light generators 607 can be in electrical communication with electronic leads 605. Electronic leads can in turn be in electrical communication with any of a number of apparatus including but not limited to a power supply or an electronic driving circuit (not shown).

It is envisioned that the switchable light source can be a dynamic light source allowing for selective and programmed excitation through one or more individual output. In one embodiment the switchable light source is an optical switch, for example, a planar optical switch. The switchable light source can be a light manipulating device for switching light from a given input to any given output. Moreover, the switchable light source can multicast an input light to several outputs all at the same time. In one embodiment, switchable light source is an optical switch coupled to a light generator through one or more optical fiber (not shown). In a particular embodiment, the light generator is coupled to one or more of the inputs of the switchable light source. By way of non-limiting examples, the light generator can provide variable wavelengths of light. In one embodiment, the light generator is a broad-band source. In another embodiment, the light generator is a tunable source.

The switchable light source can include K (=1, 2, 3 . . . ) inputs and N output. In some embodiments, the number of outputs will be equal to the number of excitation waveguides in the sensing substrate of the system. In a particular embodiment, the interface between a light generating source and the switchable light source inputs includes optical fibers. The interface between the switchable light source outputs should match, in terms of pitch, the excitation waveguides in the sensing substrate to allow these two elements to butt-couple and transfer light from the switchable light source to the excitation waveguides of the sensing substrate.

In one embodiment the optical switch includes individual switching elements based on Mach Zehnder interferometers.

The switchable light source can include an array of light generators. In one implementation, the light generators are light emitting diodes (LED). In another implementation the light generators are laser chips. Each individual light generator is separately controlled and can be turn on or off as desired. In one implementation the switchable light source includes 10 or more light generators. In another implementation the switchable light source includes 100 or more light generators. In yet another implementation the switchable light source includes 1000 or more light generators. In a particular implementation the switchable light source includes between 10 and 100 light generators.

The light generator array on the switchable light source can be integrated on a single chip which includes an array of two or more light generators and an array of two or more waveguides. In one implementation each light generator is optically coupled to one waveguide and adapted such that most of the light emitted by the light generator propagates along the waveguide. The waveguides can extend to the edge of the chip where they can be brought to couple the light propagating within them to the sensing chip. In one implementation two light generators, each optionally emitting at a different wavelength can be coupled to a single waveguide. In another implementation more than two light generators, each optionally emitting at a different wavelength can be coupled to a single waveguide.

The switchable light source can include in addition to a light generator array and waveguide array, light manipulating features such as filters, switches, modulators, splitters, combiners, mirrors and circulators.

The control of the switchable light source can be either integrated on the same chip as the light generators and waveguides or alternatively can be external to the chip. The switchable light source can have an electrical interface to an external driver or external controller or logic interface to an external control system. The control of the switchable light source allows driving each light generator separately. It further allows also control of the other features present on the switchable light source such as, for example, the modulators and switches.

The switchable light source can couple to the sensing substrate in several different ways. In one implementation the coupling is done by bringing the ends of the waveguides on both chips (the switchable light source and the sensing substrate) in close proximity and allowing the light to flow directly from one waveguide to the other. In another implementation, a portion of the waveguides on both chips are aligned on top of each other, parallel and in close proximity to each other, thus coupling light from one waveguide to the other through the evanescent electromagnetic field.

Additional elements useful in planar lightwave circuits, including but not limited to couplers, filters, mirrors, circulators, splitters, modulators, switches and trenches are envisioned as part of the system described herein (not shown). Such elements when integrated into the sensing substrate or into the switchable light source substrate can serve to manipulate both incoming first light waves in the excitation waveguides or outgoing second light waves in the collection waveguides.

Figure 7:
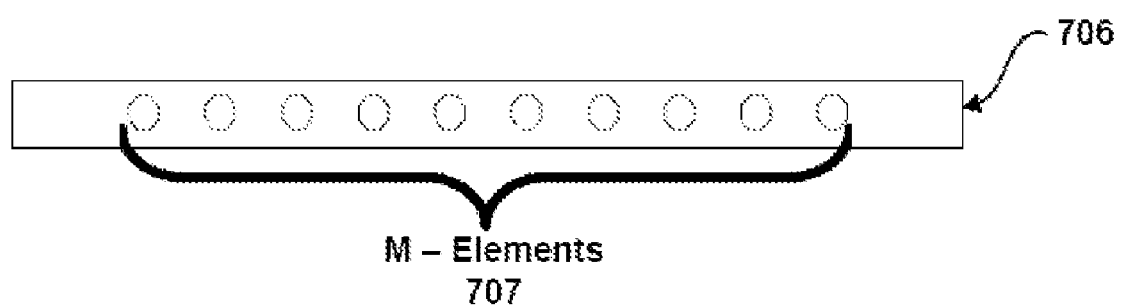
FIG. 7 is a schematic of a detector of the invention.

FIG. 7 illustrates an exemplary detector 706 of the system of the invention including elements 707 (shown as M-elements). In one embodiment, as shown in FIG. 7, the detector 706 includes an array of light sensitive elements 707, for example, in the form of a photodetector array. In one embodiment, as shown in FIG. 1A, the number of elements 116 matches the number of collection waveguides 110 in the substrate 104. Typically, the elements 116 are aligned with the collection waveguides 110 and provided in a one to one ratio.

In one non-limiting example, the detector is a detector array having a spectral range of between 400 to 1000 nm, a photosensitivity (A/W) of >0.3, an active area per element of 0.005 mm$^2$, 128 elements, and a pitch of <0.1 mm.

In one embodiment, the detector is a silicon photodiode (PN, PIN or APD) array. An example of a suitable detector array is the Texas Advanced Optoelectronic Solutions (TAOS) 1×128 linear array (PN-TSL1210R).

It is envisioned that the element size and the pitch between the elements can equal that of the collection waveguides in the substrate.

A control system for managing the different steps of operating the scanning sensing system is envisioned. The control system can manage steps such as alignment of the switchable light source, sensing substrate and detector, in addition to switching the light output from the switchable light source, reading the detector array and reporting the results detected.

In practicing the methods of the present invention, many conventional techniques in molecular biology are optionally utilized. These techniques are well known and are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5th Ed., John Wiley & Sons, Inc. (2002), Sambrook et al., Molecular Cloning: A Laboratory Manual, 3rd Ed., Cold Spring Harbor Laboratory Press (2000), and Innis et al. (Eds.) PCR Protocols: A Guide to Methods and Applications, Elsevier Science & Technology Books (1990), all of which are incorporated herein by reference.

Sample preparation suitable for use with the system and methods described herein can include any of a number of well know methods for collection and analysis of biological and/or environmental samples. In the case of biological samples the sample can be, for example, manipulated, treated, or extracted to any desired level of purity for a target of interest.

The sample can be bodily fluids suspected to contain a biologically active analyte. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

It is anticipated that the systems described herein can be used for screening a large variety of samples. In the case where the investigated subject is a living creature, the sample may originate from body fluids as discussed. Methods of obtaining samples include but are not limited to cheek swabbing, nose swabbing, rectal swabbing, skin fat extraction or other collection strategies for obtaining a biological or chemical substance. When the tested subject is a non-living or environmental body, the sample may originate from any substance in a solid phase, liquid phase or gaseous phase. The sample may be collected and placed onto the sensing substrate or the sensing substrate may be directly exposed to the investigated sample source (e.g. water reservoir, free air) and interact with it.

In some embodiments, the bodily fluids are used directly for detecting one or more biologically active analyte present therein with the subject scanning sensing device without further processing. Where desired, however, the bodily fluids can be pre-treated before performing the analysis with the subject scanning sensing devices. The choice of pre-treatments will depend on the type of bodily fluid used and/or the nature of the biologically active analyte under investigation. For instance, where the biologically active analyte is present at low level in a sample of bodily fluid, the sample can be concentrated via any conventional means to enrich the biologically active analyte. Methods of concentrating a biologically active analyte include but are not limited to drying, evaporation, centrifugation, sedimentation, precipitation, and amplification. Where the biologically active analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the biologically active analyte is a molecule present on or within a cell, extraction can be performed using lysing agents including but not limited to denaturing detergent such as SDS or non-denaturing detergent such as thesit (2-dodecoxyethanol), sodium deoxylate, Triton® X-100, and Tween® 20.

In some embodiments, pretreatment can include diluting and/or mixing the sample, and filtering the sample to remove, e.g., red blood cells from a blood sample.

Targets detectable using the scanning sensing system include but are not limited to, a biologically active analyte including a nucleic acid, a protein, an antigen, an antibody, a microorganism, a gas, a chemical agent and a pollutant.

In one embodiment, the target is a nucleic acid that is DNA, for example, cDNA. In a related embodiment, the DNA target is produced via an amplification reaction, for example, by polymerase chain reaction (PCR). In another embodiment of the subject invention, the detected biologically active analyte is a protein representing a known bio-marker for a disease or specific condition of the investigated organism. In another embodiment several different biologically active analytes can be proteins provided as a panel of bio-markers wherein relative concentrations of the bio-markers are indicative for a disease or other condition of the investigated organism. In a further embodiment the target is a microorganism that is a pathogen. In another embodiment the target is a chemical agent, for example, a toxic chemical agent.

Where the target is a nucleic acid, it can be single-stranded, double-stranded, or higher order, and can be linear or circular. Exemplary single-stranded target nucleic acids include mRNA, rRNA, tRNA, hnRNA, ssRNA or ssDNA viral genomes, although these nucleic acids may contain internally complementary sequences and significant secondary structure. Exemplary double-stranded target nucleic acids include genomic DNA, mitochondrial DNA, chloroplast DNA, dsRNA or dsDNA viral genomes, plasmids, phage, and viroids. The target nucleic acid can be prepared synthetically or purified from a biological source. The target nucleic acid may be purified to remove or diminish one or more undesired components of the sample or to concentrate the target nucleic acids. Conversely, where the target nucleic acid is too concentrated for the particular assay, the target nucleic acid may be diluted.

Following sample collection and optional nucleic acid extraction, the nucleic acid portion of the sample comprising the target nucleic acid can be subjected to one or more preparative reactions. These preparative reactions can include in vitro transcription (IVT), labeling, fragmentation, amplification and other reactions. MRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target nucleic acid. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target nucleic acid is single-stranded, the first cycle of amplification forms a primer extension product complementary to the target nucleic acid. If the target nucleic acid is single stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target nucleic acid can be amplified by contacting one or more strands of the target nucleic acid with a primer and a polymerase having suitable activity to extend the primer and copy the target nucleic acid to produce a full length complementary nucleic acid or a smaller portion thereof. Any enzyme having a polymerase activity that can copy the target nucleic acid can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB D DNA polymerases; RNA polymerases such as *E. coli*, SP6, T3 and T7 RNA polymerases; and reverse transcriptases such as AMV, M MuLV, MMLV, RNAse H' MMLV (Superscript®), Superscript® II, ThermoScript®, HIV 1, and RAV2 reverse transcriptases. All of these enzymes are commercially available. Exemplary polymerases with multiple specificities include RAV2 and Tli (exo) polymerases. Exemplary thermostable polymerases include Tub, Taq, Tth, Pfx, Pfu, Tsp, Tfl, Tli and *Pyrococcus* sp. GB D DNA polymerases.

Suitable reaction conditions are chosen to permit amplification of the target nucleic acid, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot start techniques, use of nested primers, or designing PCR primers so that they form stem-loop structures in the event of primer-dimer formation and thus are not amplified. Techniques to accelerate PCR can be used, for example, centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target nucleic acids or different regions of a particular target nucleic acid within the sample.

Amplified target nucleic acids may be subjected to post amplification treatments. For example, in some cases, it may be desirable to fragment the target nucleic acid prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow a nucleic acid associated with the optical sensing site to hybridize to the amplification product during at least part of an amplification cycle. When the assay is performed in this manner, real time detection of this hybridization event can take place by monitoring for light emission during amplification.

Real time PCR product analysis (and related real time reverse-transcription PCR) provides a well-known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" Clin Chem 45(7):982-6; Bièche et al. (1999) "Quantitation of MYC gene expression in sporadic breast tumors with a real-time reverse transcription-PCR assay" Cancer Res 59(12):2759-65; and Kreuzer et al. (1999) "LightCycler technology for the quantitation of bcr/abl fusion transcripts" Cancer Res 59(13):3171-4, all of which are incorporated by reference). In addition, linear PCR and Linear-After-The Exponential (LATE)-PCR can be adapted for use with the methods described herein.

Immunoassays can be conducted on the scanning sensor system of the invention, for example, at one or more optical sensing site of the system. Suitable immunoassay systems include but are not limited to competitive and non-competitive assay systems. Such assay systems are typically used with techniques such as western blots, radioimmunoassays, EIA (enzyme immunoassay), ELISA (enzyme-linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and cellular immunostaining (fixed or native) assays to name but a few. Such assays are routine and well known in the art (see, e.g., Ausubel et al., supra). Immunoassay techniques particularly useful with the scanning sensor systems described herein include but are not limited to ELISA, "sandwich" immunoassays, and fluorescent immunoassays. Exemplary immunoassays are described briefly below (but are not intended by way of limitation).

ELISAs generally involve preparing antigen, coating a well (e.g., an optical sensing site of the scanning sensor system) with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

In one exemplary immunoassay, a sample contains an unknown amount of biologically active analyte to be measured, which may be, for example, a protein. The analyte may also be termed an antigen. The sample may be spiked with a known or fixed amount of labeled analyte. The spiked sample is then incubated with an antibody that binds to the analyte, so that the analyte in the sample and the labeled analyte added to the sample compete for binding to the available antibody binding sites. More or less of the labeled analyte will be able to bind to the antibody binding sites, depending on the relative concentration of the unlabeled analyte present in the sample. Accordingly, when the amount of labeled analyte bound to the antibody is measured, it is inversely proportional to the amount of unlabeled analyte in the sample. The amount of analyte in the original sample may then be calculated based on the amount of labeled analyte measured, using standard techniques in the art.

In one exemplary competitive immunoassay, an antibody that binds to a biologically active analyte may be coupled with or conjugated with a ligand, wherein the ligand binds to an additional antibody added to the sample being tested. One example of such a ligand includes fluorescein. The additional antibody may be bound to a solid support (e.g., an optical sensing site of the scanning sensor system). The additional antibody binds to the ligand coupled with the antibody that binds in turn to the analyte or alternatively to the labeled analyte, forming a mass complex which allows isolation and measurement of the signal generated by the label coupled with the labeled analyte.

In another type of exemplary competitive immunoassay, the biologically active analyte to be measured may be bound to a solid support (e.g., an optical sensing site of the scanning sensor system), and incubated with both an antibody that binds to the analyte and a sample containing the analyte to be measured. The antibody binds to either the analyte bound to the solid support or to the analyte in the sample, in relative proportions depending on the concentration of the analyte in the sample. The antibody that binds to the analyte bound to the solid support is then bound to another antibody, such as anti-mouse IgG, that is coupled with a label. The amount of signal generated from the label is then detected to measure the amount of antibody that bound to the analyte bound to the solid support. Such a measurement will be inversely proportional to the amount of analyte present in the sample. Such an assay may be used in the scanning sensor system of the present invention.

A wide diversity of labels are available in the art that can be employed for conducting the subject assays. In some embodiments labels are detectable by spectroscopic, photochemical, biochemical, immunochemical, or chemical means. For example, useful nucleic acid labels include fluorescent dyes, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include enzymes, substrates, cofactors, inhibitors, fluorescent moieties, chemiluminescent moieties, or bioluminescent labels. Labeling agents optionally include, for example, monoclonal antibodies, polyclonal antibodies, proteins, or other polymers such as affinity matrices, carbohydrates or lipids. Detection proceeds by any of the methods described herein, for example, by detecting an optical signal in an optical waveguide. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Preferred labels include labels that produce an optical signal. Thus, a label includes without limitation any composition detectable by spectroscopic, photochemical, biochemical, immunochemical, electrical, optical, thermal, or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti-ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a fluorescent label, it may be detected by exciting the fluorochrome with the appropriate wavelength of light and detecting the resulting fluorescence by, for example, a scanning sensor system as described herein. Similarly, enzymatic labels are detected by providing appropriate substrates for the enzyme and detecting the resulting reaction product (e.g., a reaction product capable of producing a detectable optical signal).

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (e.g., light) when they move from an "excited state" to a lower energy state (usually the ground state); this process is often referred to as "radioactive decay". There are many causes of excitation. If the exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin allowed transitions. If photoluminescence is the result of a spin forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6, 7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In a separate embodiment, the present invention provides a method of monitoring one or more pharmacological parameter, for example, Pharmacodynamic (PD) and/or pharmacokinetic (PK) parameters, useful for assessing efficacy and/or toxicity of a therapeutic agent. The method comprises subjecting a sample of bodily fluid from a subject administered with the therapeutic agent to a scanning sensing device for monitoring the one or more pharmacological parameter, the scanning sensing device can be used as described herein to yield detectable signals indicative of the values of the more than one pharmacological parameter from the sample; and detecting the detectable signal generated from said sample of bodily fluid.

In one implementation the samples tested can include a large number of a variety of small molecules (e.g., screening libraries) which are of interest when investigating new drugs. Accordingly, the scanning sensing system described herein is useful for screening libraries of small molecules to investigate their ability to interact with certain biologically active analytes may reveal potential new drugs. Further screening of some or all small molecule candidates may reveal adverse drug effects and toxicity.

In one implementation the samples can include molecules which are tested for toxicity.

In general in another aspect methods of using the scanning sensing system described herein are provided. In one embodiment, the switchable light source, for example, an optical switch or an array of light generators, couples light into one or more excitation waveguides at any given time. The light travels along the excitation waveguides, reaches the optical sensing sites and interacts through the sensor, for example, an optical transducer. The samples are positioned at or near the excitation waveguides. Next, the light leaving the sensor couples into the collection waveguides and travels down the waveguide to its end at an edge of the substrate, for example, a chip facet. Light exiting the collection waveguides is then detected by the different elements of the detector, which can be a detector array.

In another embodiment, scanning sensing of a sample includes delivering a sample suspected of containing a target to be detected to an optical sensing site of the scanning sensor system. Delivering a sample to the system can include pipetting of a fluid to the optical sensing site. Other delivery means can include but are not limited to robotic fluid delivery system or physically depositing a non-fluid or semi-fluid sample at the optical sensing site, either by hand or with the aid of a tool or robot manipulation system. Next, a first light wave produced by the switchable light source is provided to one or more of the plurality of substantially parallel excitation waveguides in optical communication with the optical sensing site. The first light wave is transduced (e.g., measurably changed) by the sensor associated with the optical sensing site to form a second light wave carried in one or more of the plurality of substantially parallel collection waveguides which are in optical communication with the optical sensing site and cross the excitation waveguides. Next a measurable change in the second light wave is detected using the detector which is in optical communication with the collection waveguides. Detection of measurable change in the second light waves indicates that the sensor has interacted with the target.

In a further embodiment, scanning sensing includes switching one or more light wave from the switchable light source into the substrate to produce the first light wave in one or more of the excitation waveguides in a controlled and scanning manner.

In another embodiment, the switchable light source comprises an optical switch for controlling switching of one or more input light wave. The optical switch can multicast light to a plurality of outputs. The plurality of light waves can be coupled into the sensing substrate to controllably produce the first light wave in one or more of the excitation waveguides.

In one embodiment, a single excitation waveguide is provided with a first light wave and simultaneous detection of second light waves at each collection waveguide is achieved using a detector that is a photodetector array. By switching light between excitation waveguides, each individual excitation waveguide can be individually addressed with a first light wave. The order of addressing the excitation waveguides can be sequential, staggered, random or in any order desired. Rapid scanning of the entire two-dimensional array of optical sensing sites can be achieved with the aid of the photodetector array since any second light wave associated with each collection waveguide can be simultaneously detected. For example, where the two-dimensional array is configured as an array of 128 excitation waveguides and 128 collection waveguides, then it would be possible to simultaneously detect second light waves (if any) generated from 128 optical sensor sites after providing a single first lightwave in a first excitation waveguide. Thus, 128 optical sensing sites can be interrogated for presence or absence of target simultaneously. Next, a second excitation waveguide can be excited thereby triggering the interrogation of a second set of 128 optical sensing sites. The process can rapidly be repeated until every excitation waveguide has been excited and the entire array of optical sensing sites have been interrogated.

In various embodiments the method of using the scanning sensing system involves the detection of a substance, including but not limited to a biologically active analyte including a nucleic acid, a protein, an antigen, an antibody, a panel of proteins, a microorganism, a gas, a chemical agent and a pollutant. In a particular embodiment, a single nucleotide polymorphism (SNP) is detected in the target. In one embodiment expression of a gene is detected upon detection of the target.

In one embodiment immunoassays can be used with the present method of using the scanning sensing system. The sensor of the method of using the scanning sensing system of the invention can be adapted to support an immunoassay, for example, by including one or more immunoassay reagent at or within the sensor. In this embodiment an interaction between the sensor and a sample being tested for a biologically active analyte can include an immunoassay conducted at the sensor. As such, the sensor interacting with the biologically active analyte can include an outcome of an immunoassay. In this manner, presence or absence of the analyte can be determined. Additionally the amount of analyte can be quantified. In one embodiment the immunoassay supported is a fluorescent assay. It is envisioned that the immunoassay can be a competitive or non-competitive immunoassay. In one embodiment the immunoassay supported in an ELISA.

It is envisioned that a variety of instrumentation relating to biological or environmental sample preparation, handling and analysis can be used in conjunction with the system and methods described herein. Examples of such instrumentation include but are not limited to a cell sorter, a DNA amplification thermal cycler, or a chromatography machine (e.g., GC or HPLC). Such instrumentation is well known to those skilled in the art. It is envisioned that a robotic interface could be used between the scanning sensing system of the present invention and various instrumentation relating to biological or environmental sample preparation, handling and analysis.

The system and methods described herein may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis or diagnosis of HIV, as disclosed in U.S. Pat. No. 6,027,880 and U.S. Pat. No. 5,861,242. Genetic mutations may be detected by sequencing by hybridization. In one embodiment, genetic markers may be sequenced and mapped using Type-IIs restriction endonucleases as disclosed in U.S. Pat. No. 5,710,000.

Other applications include chip based genotyping, species identification and phenotypic characterization, as described in U.S. Pat. No. 6,228,575. Still other applications including diagnosing a cancerous condition or diagnosing viral, bacterial, and other pathological or nonpathological infections, are described in U.S. Pat. No. 5,800,992. A further application includes chip based single nucleotide polymorphism (SNP) detection as described in U.S. Pat. No. 6,361,947.

Gene expression may be monitored by hybridization of large numbers of mRNAs in parallel using high density arrays of nucleic acids in cells, such as in microorganisms such as yeast, as described in Lockhart et al., Nature Biotechnology, 14:1675-1680 (1996). Bacterial transcript imaging by hybridization of total RNA to nucleic acid arrays may be conducted as described in Saizieu et al., Nature Biotechnology, 16:45-48 (1998). Accessing genetic information using high density DNA arrays is further described in Chee, Science 274:610-614 (1996).

A non-limiting list of potential application suitable for sensing using the systems and methods described herein includes: pathogens detection and classification; chemical/biological warfare real-time detection; chemical concentration control; dangerous substance (e.g., gas, liquid) detection and alarm; sugar and insulin levels detection in diabetic patients; pregnancy testing; detection of viral and bacterial infectious diseases (e.g. AIDS, Bird Flu, SARS, West Nile virus); environmental pollution monitoring (e.g., water, air); and quality control in food processing.

The working system described here can also be a subsystem within a much larger bio-analysis system. The bio-analysis system could include all the aspects of sample preparation prior to the optical scanning, the post processing of data collected in the optical scanning phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and spotting of the sample into the sensing chip. The post processing of the collected data may include: normalization; background and noise reduction; and statistical analysis such as averaging over repeated tests or correlation between different tests. The decision making may include: testing against a predefined set of rules and comparison to information stored in external data-bases.

The applications and uses of the scanning sensing systems described herein can produce one or more result useful to diagnose a disease state of an individual, for example, a patient. In one embodiment, a method of diagnosing a disease comprises reviewing or analyzing data relating to the presence and/or the concentration level of a target in a sample. A conclusion based review or analysis of the data can be provided to a patient, a health care provider or a health care manager. In one embodiment the conclusion is based on the review or analysis of data regarding a disease diagnosis. It is envisioned that in another embodiment that providing a conclusion to a patient, a health care provider or a health care manager includes transmission of the data over a network.

Accordingly, business systems and methods using the scanning sensing systems and methods described herein are provided.

One aspect of the invention is a business method comprising screening patient test samples for the presence or absence of a biologically active analyte to produce data regarding the analyte, collecting the analyte data, providing the analyte data to a patient, a health care provider or a health care manager for making a conclusion based on review or analysis of the data regarding a disease diagnosis. In one embodiment the conclusion is provided to a patient, a health care provider or a health care manager includes transmission of the data over a network.

Figure 8:
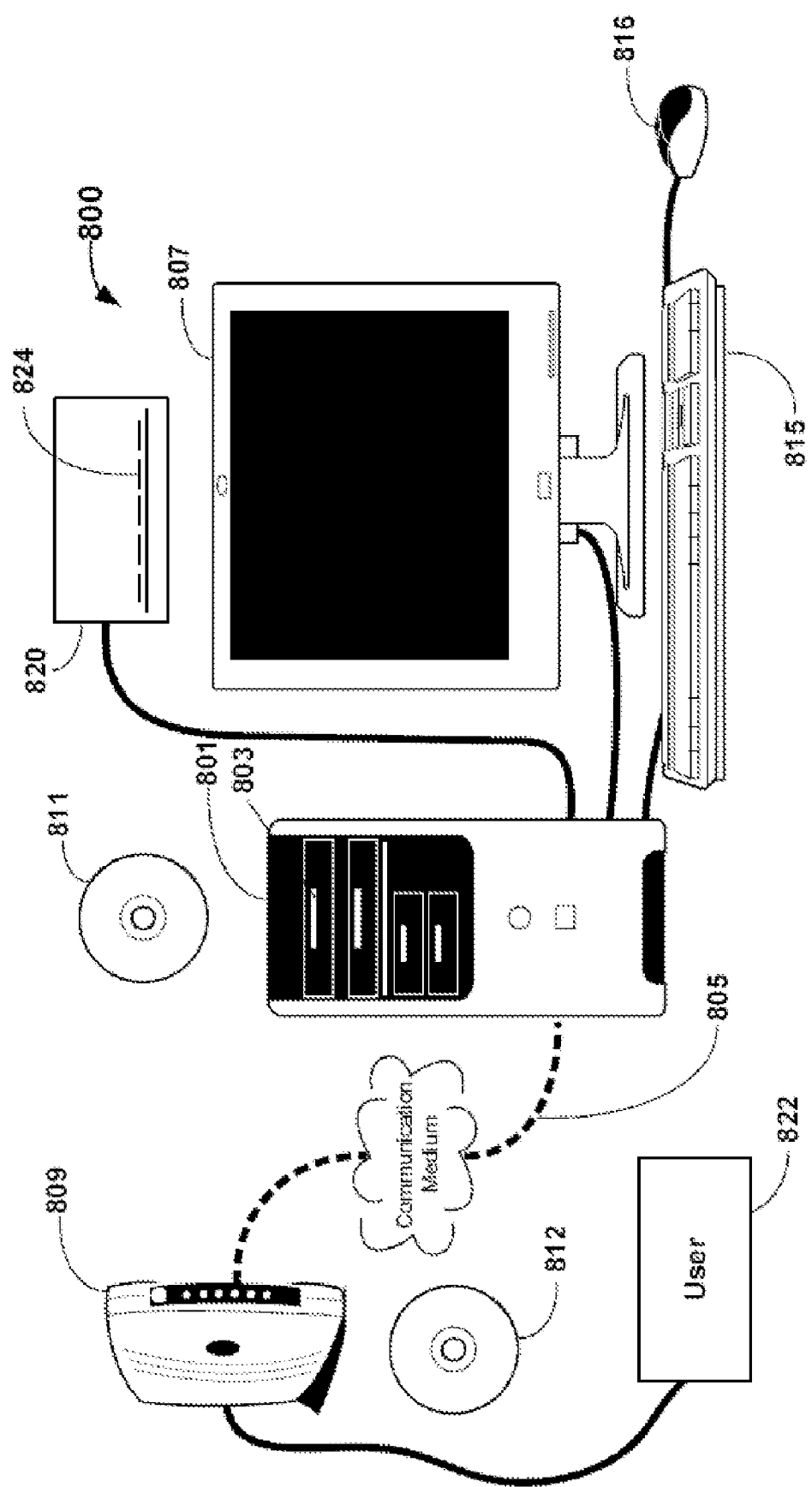
FIG. 8 is a block diagram showing a representative example logic device in communication with an apparatus for use with the scanning sensing system of the invention.

Accordingly FIG. 8 is a block diagram showing a representative example logic device through which reviewing or analyzing data relating to the present invention can be achieved. Such data can be in relation to a disease, disorder or condition in an individual. FIG. 8 shows a computer system (or digital device) 800 connected to an apparatus 820 for use with the scanning sensing system 824 to, for example, produce a result. The computer system 800 may be understood as a logical apparatus that can read instructions from media 811 and/or network port 805, which can optionally be connected to server 809 having fixed media 812. The system shown in FIG. 8 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 822. The receiving party 822 can be but is not limited to a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein.

Kits comprising reagents useful for performing the methods described herein are also provided.

In some embodiments, a kit comprises scanning sensing system as described herein and reagents for detecting a target in the sample. The kit may optionally contain one or more of the following: one or more fluorescent or luminescent molecular tag, and one or more biologically active analyte including a nucleic acid, protein, microorganism or chemical agent.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target biologically active analyte including nucleic acid, protein, microorganism, gas, chemical agent or pollutant.

Figure 9:
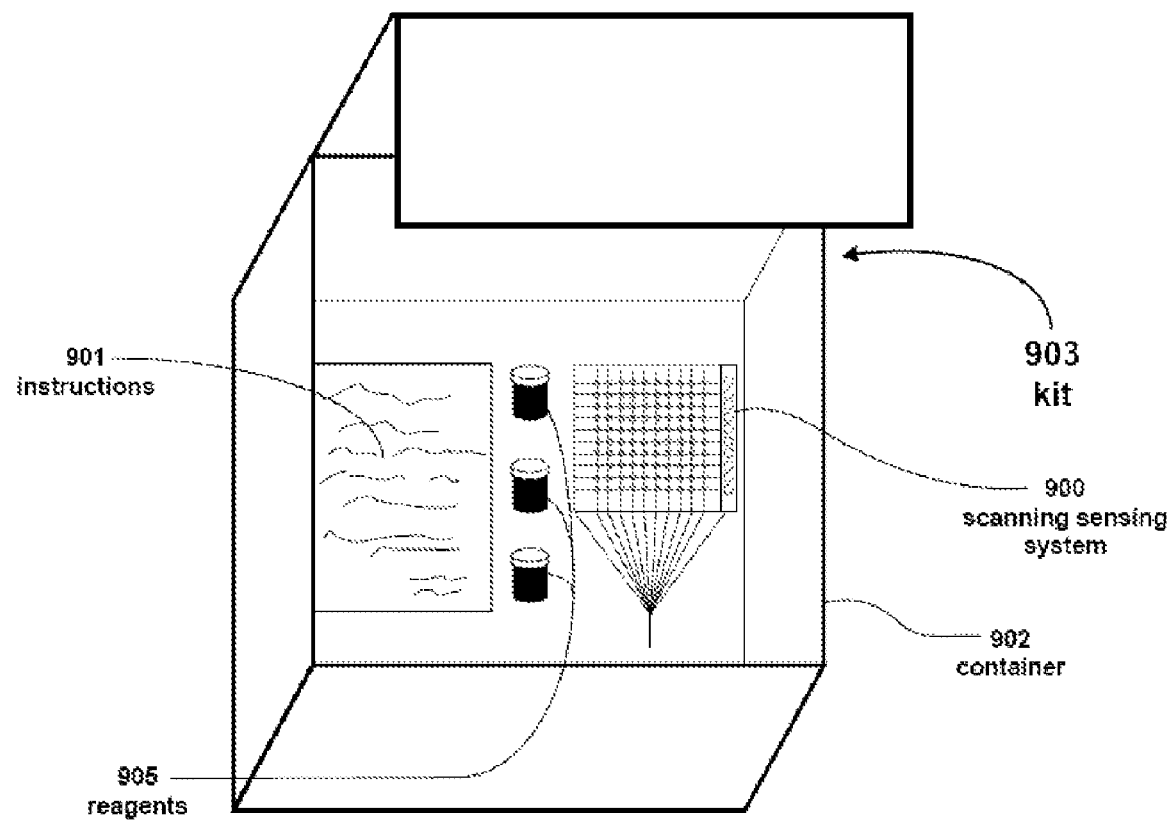
FIG. 9 is a block diagram showing a representative example of a kit.

As described herein and shown in an illustrative example in FIG. 9, in certain embodiments a kit 903 can include a housing or container 902 for housing various components. As shown in FIG. 9, and described herein, the kit 903 can optionally include instructions 901 and reagents 905, for example, DNA hybridization or immunoassay reagents. Other embodiments of the kit 903 are envisioned wherein the components include various additional features described herein.

In one embodiment, a kit for assaying a sample for a target includes a scanning sensor system including a switchable light source, a detector, and a substrate. The substrate includes a plurality of substantially parallel excitation waveguides and a plurality of substantially parallel collection waveguides. The excitation waveguides and collection waveguides of the substrate cross or intersect to form intersection regions and a two-dimensional array. The system further includes a plurality of optical sensing sites including sensors. The optical sensing sites are in optical communication with one or more excitation waveguides and one or more collection waveguides. The kit further includes packaging and instructions for use of the system.

In one embodiment, the kit includes a scanning sensor system that is a planar lightwave circuit. In another embodiment, the crossing of the excitation waveguides and collection waveguides is substantially perpendicular.

In general, in another aspect methods of manufacturing a scanning sensing system for assaying a sample for a target are provided. In one embodiment the system is a planar lightwave circuit (PLC).

The starting material or substrate for manufacturing PLC devices is a wafer usually made of Silicon (Si) or Silica (SiO2). The most common wafer diameters in use are 4", 6" and 8". The manufacturing process for PLC devices involves two basic processes namely, deposition and etching. A short description of each of them is given below.

In certain embodiments the methods of manufacturing the systems described herein can include, but are not limited to laser writing, UV writing and photonic band-gap waveguide methods. The manufacturing process in some embodiments includes one or more steps of deposition, masking and etching.

Deposition

In the deposition step a layer of well defined material having well controlled thickness is deposited across the entire wafer. The most common material used for waveguide layer deposition is Silica (SiO2) also known as glass. The optical properties of the Silica (mainly its refractive index) is controlled by the amount of doping (Ge, P, and B etc.) introduced during the deposition. Other materials such as silicon, glass, epoxy, lithium niobate, indium phosphide and SiON (Silicon OxyNitride) and its derivatives are also used. For the cladding layer, materials can include but are not limited to silicon, silica (SiO2), glass, epoxy, lithium niobate and indium phosphide The deposition step is done using several technologies such as PECVD (Plasma-Enhanced Chemical Vapor Deposition), LPCVD (Low Pressure CVD), APCVD (Atmospheric pressure CVD), FHD (Flame Hydrolysis Deposition) and others well known in the art.

Figure 10:
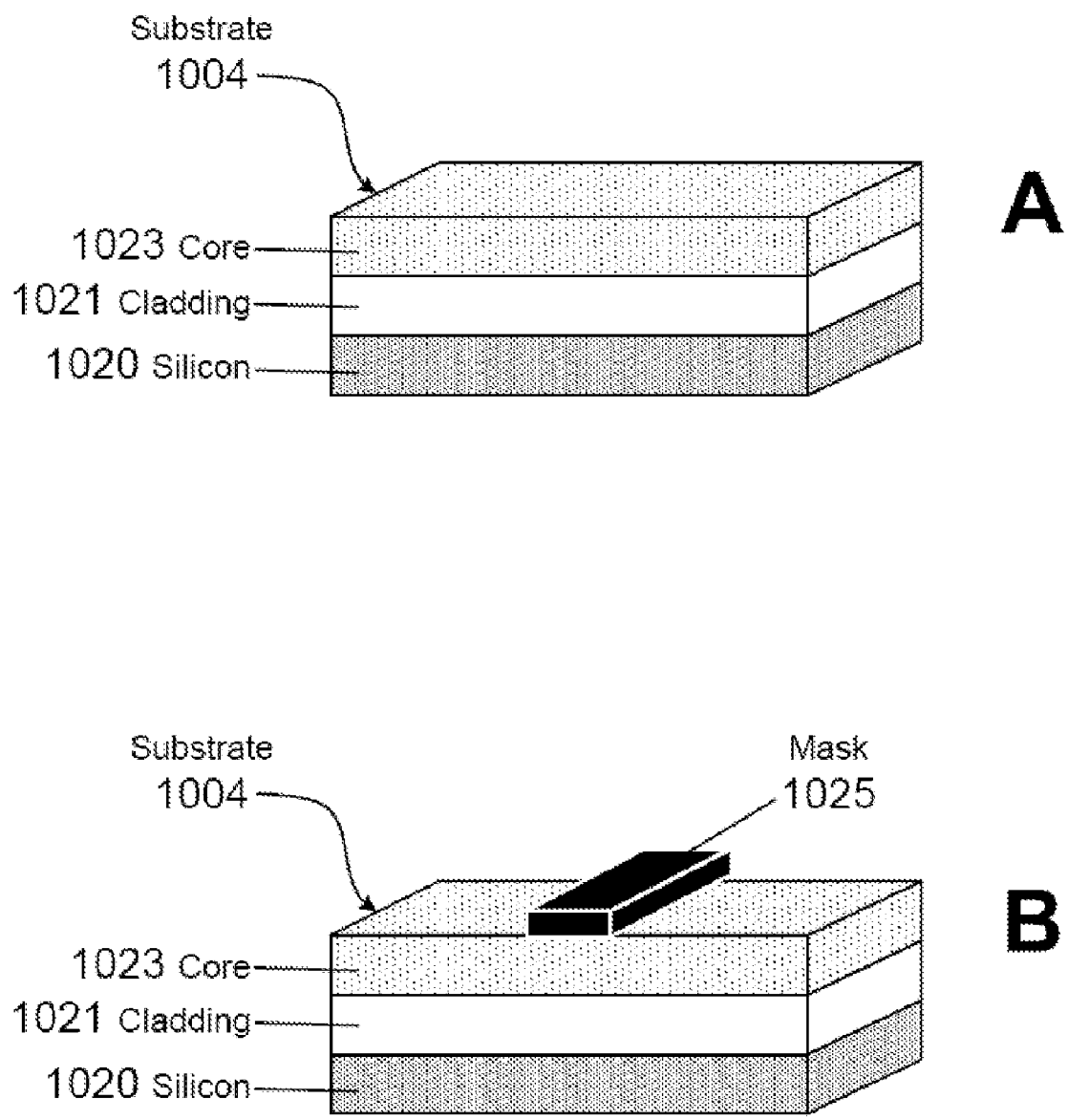
FIGS. 10A-D are schematics illustrating a representative manufacturing process for the substrate and waveguides of the invention.
Figure 10:
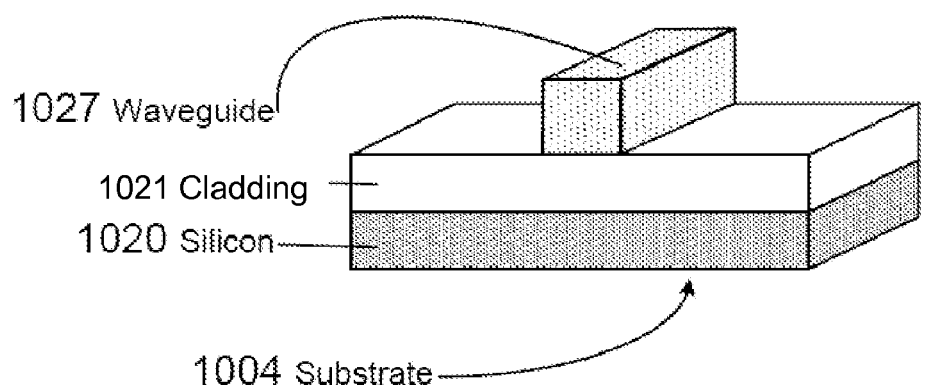
Figure 10:
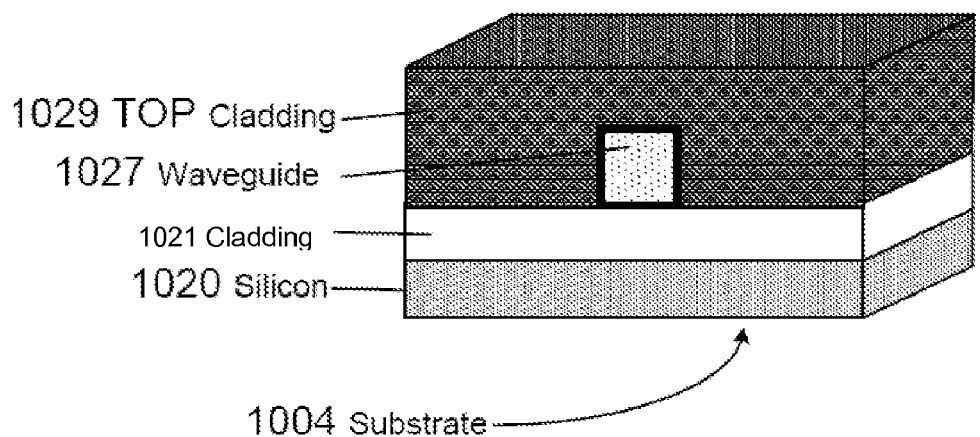

FIG. 10A illustrates an exemplary substrate 1004 as a schematic structure created after two consecutive deposition steps of a cladding 1021 layer and a core 1023 layer over a silicon 1020 layer, which can be a wafer. As mentioned above, these two layers differ in the refraction index which is achieved by using different levels of doping. Typical thicknesses for the different layers are: Cladding up to about 20 μm and core up to 6 μm. The thickness of the silicon 1020 wafer can range from about 0.5 mm to 1 mm.

Masking

Following the deposition and before the etching step, the desired two-dimensional structure of the PLC device is transferred to the deposited wafer by masking the areas not to be etched away. The masking is done in several steps involving covering the wafer with light sensitive material, exposing it to light through lithographic masks and removing the exposed material leaving in place the mask. The result of such steps is shown in FIG. 10B where a mask 1025 is shown on top of the core 1023 layer of the substrate 1004.

Etching

In the etching step, material at the un-masked areas is removed from the top core 1023 layer of the substrate (see FIG. 10C). The etching rate is a known parameter, therefore the etching depth can be controlled by time. The two most common techniques for etching are wet-etching and Reactive-Ion-Etching (RIO). FIG. 10C shows the results of the etching step which results in a waveguide 1027.

After the etching step, an over-cladding or top cladding 1029 layer is created using a deposition step similar to the one described above. The results are shown in FIG. 10D. As shown in FIG. 10D, the resulting waveguide 1027 can be surrounded by a top cladding 1029 and a cladding 1021 over a silicon 1020 layer.

The above steps can be repeated to create several waveguide layers one on top of the other (see for example, FIG. 3). In this case, a planarization step is required between one waveguide layer and the other. This is done using a technique known as Chemical Mechanical Planarization (CMP).

Figure 11:
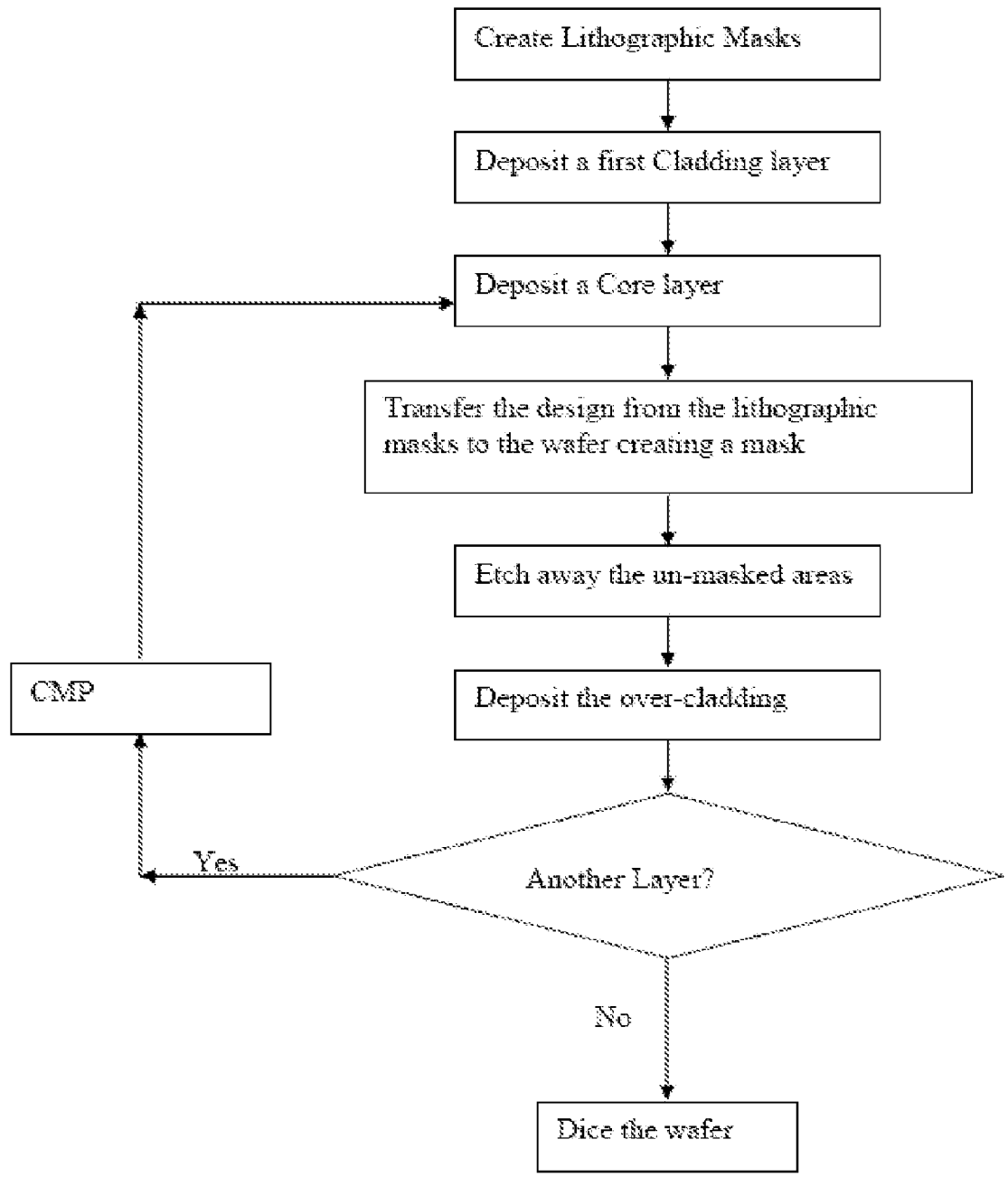
FIG. 11 is a flow chart showing a representative manufacturing process for the substrate.

When the wafer processing is completed, it can be diced into the individual chips. An exemplary simplified flow-chart of the manufacturing process is shown in FIG. 11.

EXAMPLES

Prophetic Example 1

Quantitative real-time PCR detection of transcripts, for example, bcr/abl fusion transcripts, can be achieved using a scanning sensing system such as the example illustrated in FIG. 1A using a PCR assay protocol modified from that described by Kreuzer et al. (supra). The system includes a substrate chip with excitation waveguides, collection waveguides and intersection regions. The intersection regions where the excitation waveguides and collection waveguides cross include optical sensing sites with sensing wells for conducting quantitative real-time PCR. The scanning sensing system further includes a dynamic switchable light source coupled to the substrate and the excitation waveguides. The system further includes an optical detector.

Samples suspected of containing RNA transcripts of interest (e.g., blood from a subject) are treated to obtain a source of total RNA which is subsequently reverse transcribed using reverse transcriptase into cDNA using techniques well known in the art. cDNA samples are delivered to sensing sites on the substrate of the system. As desired, suitable controls and different dilutions of a particular cDNA sample can be delivered to different sensing wells.

Reagents for real-time reverse transcriptase PCR are provided at the sensing sites. PCR reactions are conducted using primers/probes specific for one or more bcr/abl breakpoint cluster region. Such primers/probes are well known in the art (e.g., see Kreuzer et al. supra) and can be labeled with 6-carboxy-fluorescein phosphoramidite at the 5' end, and as a quencher, 5-carboxy-tetramethyl-rhodamine can be incorporated further along the primers/probes sequence. As the probe is hydrolyzed through the 5'-nucelase activity of Taq DNA polymerase, unquenched fluorescence from the fluorescein (reporter) dye can be induced. Phosphate groups are attached to primers/probes 3' end to prevent probe extension. A 10-µl PCR reaction mix contained 1 µl of 10× PCR buffer, 4.5 mM MgCl2, 0.8 mM dNTP, 0.5 µM each primer, 1 µM probe, 0.2 units of a temperature-release Taq DNA polymerase (Platinum® Pfx DNA Polymerase; Invitrogen, Corp.), and 20 ng of sample cDNA. PCR amplification is started with a 5-min denaturation step at 94° C., followed by 45 cycles of denaturation at 94° C. for 30 s and annealing/extension at 65° C. for 60 s.

While PCR amplification proceeds excitation light at a wavelength of about 472 nm is generated by the switchable light source and is directed to each sensing well by the excitation waveguides. If the cDNA samples included a transcript for bcr/abl fusion transcripts, annealing of primers/probes to the cDNA should occur. Subsequent hydrolysis of the probe by polymerase and unquenching of the fluorescein reporter results in fluorescence in the sensing well. As the number of cycles increases, the amount of unquenched fluorescein increases in relation to the amount of bcr/abl fusion transcript cDNA in the reaction.

By way of the collection waveguides fluorescence in the sensing wells is detectable by the optical detector of the system. Thus, detection of bcr/abl fusion transcripts can be measured in real-time and based on appropriate controls and analysis the amount of bcr/abl fusion transcripts in a sample can be quantified.

Prophetic Example 2

Fluorescent immunoassay-based detection of HIV+ status of multiple subjects can be achieved using a scanning sensing system such as the example illustrated in FIG. 1A. The system includes a substrate chip with excitation waveguides, collection waveguides and intersection regions. The intersection regions where the excitation waveguides and collection waveguides cross include optical sensing sites with sensing wells for conducting fluorescent immunoassays. The scanning sensing system further includes a dynamic switchable light source coupled to the substrate and the excitation waveguides. The system further includes an optical detector.

A partially purified antigen, for example, inactivated HIV protein p29 antigen, is pre-coated onto the sensing wells of the optical sensing sites. Next, a number subject serums which may contain antibodies to HIV p29 are delivered to separate sensing sites. If a subject is HIV+, then their serum may contain antibodies to HIV protein p29, and those antibodies will bind to the HIV p29 antigens on the sensing sites. After a washing step, anti-human immunoglobulin coupled to a fluorescent dye (fluorescein) is added to the sensing sites. This secondary antibody, binds to human antibodies in the sensing sites (i.e., the anti-p29 antibodies). Next an excitation light at a wavelength of about 472 nm is generated by the switchable light source and is directed to each sensing well by the excitation waveguides. If the secondary antibody is present the coupled fluorescein will fluoresce in the presence of the excitation light in the well.

By way of the collection waveguides fluorescence in the sensing wells is detectable by the optical detector of the system. Signal received by the optical detectors can be interpreted to determine if a given subject had antibodies to HIV p29. Suitable controls can be used to validate results of the assay. Thus, the presence or absence of HIV p29 can be measured in a sample and HIV+ or HIV(−) status of multiple subjects can be determined.

Prophetic Example 3

A two-site sandwich immunoassay can be employed in assays using the scanning sensing system of the invention (e.g., the system as illustrated in FIG. 1A). Antibodies fulfill two different roles in such assays; an immobilized antibody captures the analyte, while a soluble, fluorescently labeled antibody detects or "traces" analyte binding. To prevent competitive binding, capture and tracer antibodies must bind to different sites on the analyte molecule. For large analytes with repetitive epitopes (e.g., viruses and bacteria), a single antibody (specific for the repetitive epitope) can usually be employed in both capture and tracer roles. Smaller analytes (e.g. proteins and polysaccharides) expressing multiple, unique epitopes require two different antibodies, each specific for a unique epitope.

Three two-site sandwich immunoassay tests are envisioned: 1) serial testing of optical sensing sites; 2) low complexity parallel testing of optical sensing sites; and 3) sensitivity testing. In the first of these, a small volume (1-5 µL) of sample (containing analyte and tracer antibody) is spotted directly at a optical sensing site containing capture antibody using a microliter pipette. Binding kinetics at the site are monitored over a 5-min period at room temperature. Translation of optical detection to excitation and collection waveguides in connection with a different optical sensing site is effected and the assay is repeated at the new site. It is envisioned that at least 10 optical sensing sites can be tested using this serial procedure. Such tests can demonstrate sensitivity and intra-assay precision of the system.

In the second form of testing using a substrate of the system that includes a 10×10 array of excitation waveguides and collection waveguides (see e.g., FIG. 1A), a single excitation waveguide of the substrate is excited, while output signals are monitored from all 10 collection waveguides using either an optical switch or a linear array of photodiodes. Equal volumes (e.g., 50 µL) of sample containing analyte and tracer antibody (e.g., 10 nM, final concentration) can be pre-mixed and then injected into a sample well of the optical sensing site that contains capture antibody. Binding kinetics are monitored simultaneously in 10 optical sensing sites over a 5-min period at room temperature. This form of testing can demonstrate the parallel assay capabilities of the system, as well as providing more detailed information about intra-assay precision.

In the third form of testing the sensitivity, precision and linearity of the device can be demonstrated by constructing a standard curve of average reaction rate versus analyte concentration. Device configuration is the same as described above for the second form of testing (i.e., 10 simultaneous assays). Analyte concentration is varied over at least a 100-fold range, e.g. 10 pM to 1 nM, though the exact range can be adjusted depending on the clinical concentration range of the analyte being examined. A separate substrate chip is used for each concentration to be tested. Six to eight concentrations are examined. Resulting standard curves are typically linear at low concentration, but saturate at higher concentrations.

The Herron lab has developed immunoassays for many different analytes including human cardiac troponin I (cTnI), chorionic gonadotrophin (hCG), creatine phosphokinase isoform MB (CKMB), myoglobin, ovalbumin (used by the military as a "simulant" for toxins such as ricin and SEB), ricin, *Staphylococcal* enterotoxin B (SEB). (see: Herron, J. N., H.-K. Wang, V. Janatová, J. D. Durtschi, K. D. Caldwell, D. A. Christensen, I. -N. Chang and S.-C. Huang (2003). Orientation and Activity of Immobilized Antibodies. In: Biopolymers at Interfaces, 2nd Edition (M. Malmsten, ed.), Surfactant Science Series, Vol. 110, Marcel Dekker, New York, pp. 115-163; and Herron, J. N., H.-K. Wang, V. Janatová, J. D. Durtschi, K. D. Caldwell, D. A. Christensen, Durtschi, E. M. Simon, M. E. Astill, R. S. Smith and D. A. Christensen (2005). Planar Waveguide Biosensors for Point-Of-Care Clinical and Molecular Diagnostics. In: Fluorescence Sensors and Biosensors (R. B. Thompson, Ed.). CRC Press Taylor & Francis Group, Boca Raton, Fla. pp. 283-332)

The ovalbumin assay of Herron can be used in the first and second immunoassays described above. Advantageously, reagents for this assay are relatively inexpensive and no special handling is required. Detection requirements for cTnI and SEB are the most stringent, and thus immunoassays specific for these analytes are useful for the sensitivity testing immunoassays. However, since the CDC, NIH, and USDA all list SEB as a select agent requiring special handling it may be preferable to use cTnI in sensitivity testing. cTnI can be paired with two other cardiac markers (CKMB and myoglobin) for simultaneous immunoassay sensitivity testing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A scanning sensor system for detecting a biologically active analyte comprising:
   a switchable light source;
   a detector;
   a substrate coupled to and in optical communication with the switchable light source and the detector, wherein the substrate comprises a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing; and
   a plurality of optical sensing sites each in optical communication with an intersection region.

2. The system of claim 1, wherein the system is substantially planar.

3. The system of claim 1, wherein the system comprises a planar lightwave circuit.

4. The system of claim 1, wherein the switchable light source is coupled to and in communication with one or more of the excitation waveguides at a first edge of the substrate and the detector is coupled to and in communication with one or more of the collection waveguides at a second edge of the substrate.

5. The system of claim 1, wherein the optical sensing sites comprise a sensor and a sample comprising a biologically active analyte, wherein a measurable change in a first light wave results when the sensor discriminates or interacts with the biologically active analyte.

6. The system of claim 5 wherein a first light wave generated by the switchable light source in an excitation waveguide is transduced by a sensor of an optical sensing site in optical communication with the excitation wave guide resulting in a second light wave in a collection waveguide, the second light wave being detectable by the detector.

7. The system of claim 1, wherein the sensor is adapted to support an immunoassay.

8. The system of claim 7, wherein the immunoassay supported is an enzyme-linked immunosorbent assay (ELISA).

9. The system of claim 7, wherein the immunoassay supported is a fluorescent immunoassay.

10. The system of claim 1, wherein the sensor is selected from the group consisting of a fluorescence well, an absorption cell, an interferometric sensor, a diffractive sensor and surface plasmon resonance sensor.

11. The system of claim 1, wherein the biologically active analyte is selected from the group consisting of a nucleic acid, a protein, an antigen, an antibody, a microorganism, a gas, a chemical agent and a pollutant.

12. The system of claim 11, wherein the nucleic acid is produced via an amplification reaction.

13. The system of claim 1, wherein the excitation waveguides are single-mode and the collection waveguides are multi-mode.

14. The system of claim 1, wherein the excitation waveguides support single-mode in a first vertical dimension and multi-mode in a second lateral dimension and wherein the collection waveguides are multi-mode.

15. The system of claim 1, wherein the excitation waveguides and the collection waveguides are multi-mode.

16. The system of claim 1, wherein the excitation waveguides and the collection waveguides are single-mode.

17. The system of claim 1, wherein the excitation waveguide comprises a plurality of branches for drawing a fraction of the light from a first light wave traveling in the excitation waveguide.

18. The system of claim 17, wherein the excitation waveguide branches are in optical communication with the excitation waveguide.

19. The system of claim 1, wherein the collection waveguide comprises a plurality of funnels for collecting light from the sensing sites and coupling it to the collection waveguide.

20. The system of claim 1, wherein the optical sensing sites comprise wells.

21. The system of claim 1, wherein the optical sensing sites comprise the surface of the substrate above the intersection region of the excitation waveguides and the collection waveguides.

22. The system of claim 1, wherein the optical sensing sites comprise biochemical interaction sites.

23. The system of claim 1, wherein the optical sensing sites comprise optical transducers.

24. The system of claim 23, wherein the optical transducers comprise fluorescence wells comprising fluorescent or luminescent compounds, wherein light waves guided by the excitation waveguides excite the fluorescent or luminescent compound in the wells in the presence of a biologically active analyte, and the collection waveguides collect and guide light emitted from the wells to the detector.

25. The system of claim 1, wherein the switchable light source comprises a dynamic light source.

26. The system of claim 1, wherein the switchable light source comprises a chip containing an array of light generators coupled to an array of waveguides.

27. The system of claim 1, wherein the switchable light source is an optical switch comprising a light generator coupled to one or more input of the optical switch.

28. The system of claim 27, wherein the optical switch further comprises a branched architecture.

29. The system of claim 28, wherein the optical switch further comprises one or more inputs and multiple outputs.

30. The system of claim 29, wherein the optical switch further comprises greater than about 10 outputs.

31. The system of claim 29, wherein the optical switch further comprises greater than about 100 outputs.

32. The system of claim 29, wherein the optical switch further comprises greater than about 1,000 outputs.

33. The system of claim 29, wherein the optical switch further comprises substantially between 50 and 500 outputs.

34. The system of claim 1, wherein the switchable light source is butt-coupled to the substrate.

35. The system of claim 1, wherein the switchable light source comprises one or more waveguide and is evanescently coupled to the substrate through a proximate arrangement of the one or more switchable light source waveguide and one or more excitation waveguide of the substrate.

36. The system of claim 27, wherein the light generator provides variable wavelengths of light.

37. The system of claim 27, wherein the light generator is selected from the group consisting of a broad-band source, a source with one or more discrete spectral lines and a tunable source.

38. The system of claim 1, wherein the detector is a photodetector array.

39. The system of claim 1, wherein the detector is a plurality of detectors.

40. The system of claim 39, wherein two or more detectors are coupled to and in optical communication with one or more of the collection waveguides or the excitation waveguides at one or more edges of the substrate.

41. The system of claim 1, wherein the number of intersection regions is greater than 10.

42. The system of claim 1, wherein the density of intersection regions is greater than 100 per $cm^2$.

43. The system of claim 1, wherein the density of intersection regions is greater than 2,000 per $cm^2$.

44. The system of claim 1, wherein the system further comprises a thermal transfer element in thermal communication with the substrate.

45. The system of claim 44, wherein the thermal transfer element is a thermoelectric cooler.

46. The system of claim 1, wherein each optical sensing site comprises a thermal transfer element in thermal communication with the optical sensing site.

47. The system of claim 46, wherein the thermal transfer element comprises a thin-film heater.

48. The system of claim 46, wherein each optical sensing site further comprises a thermistor in thermal communication with the optical sensing site.

49. The system of claim 1, wherein the substrate further comprises one or more microchannel and one or more reservoirs in fluid communication with one or more optical sensing site.

50. The system of claim 1, wherein the system further comprises a fluidics layer coupled to the substrate and comprising one or more microchannel and one or more reservoirs in fluid communication with one or more optical sensing site.

51. A scanning sensing method comprising:
    delivering a sample suspected of containing a biologically active analyte to be detected to an optical sensing site of a scanning sensor system;
    providing a first light wave using a switchable light source to one or more of a plurality of substantially parallel excitation waveguides in optical communication with the optical sensing site, wherein the first light wave is transducable by a sensor associated with the optical sensing site to a second light wave carried in one or more of a plurality of substantially parallel collection waveguides in optical communication with the optical sensing site and crossing the excitation waveguides; and
    detecting a measurable change in the second light wave using a detector in optical communication with the collection waveguides, wherein a measurable change in the first light waves occurs when the sensor interacts with the biologically active analyte.

52. The method of claim 51, wherein scanning sensing further comprises switching one or more input light wave from the switchable light source into the substrate to produce the first light wave in one or more of the excitation waveguides.

53. The method of claim 51, wherein the switchable light source comprises an optical switch for controlled switching of one or more input light wave, the optical switch can multicast light to a plurality of outputs and into the substrate to controllably produce the first light wave in one or more of the excitation waveguides.

54. The method of claim 51, wherein the switchable light source comprises an array of individually controlled light generators for controlled switching of one or more input light wave, to controllably produce the first light wave in one or more of the excitation waveguides.

55. The method of claim 51, further comprising simultaneously detecting the second light wave with the detector at the end of each collection waveguide wherein the detector comprises a photodetector array.

56. The method of claim 51, wherein, a portion of the sensing sites comprise reference sample material for calibration and/or normalization.

57. The method of claim 51, wherein the biologically active analyte is selected from the group consisting of a nucleic acid, a protein, an antigen, an antibody, a microorganism, a gas, a chemical agent and a pollutant.

58. The method of claim 51, wherein the biologically active analyte is a protein.

59. The method of claim 51, wherein a SNP is detected in the biologically active analyte.

60. The method of claim 51, wherein expression of a gene is detected upon detection of the biologically active analyte.

61. The method of claim 51, wherein the sensor is adapted to support an immunoassay and wherein the sensor interacting with the biologically active analyte comprises an outcome of an immunoassay.

62. The method of claim 61, wherein the immunoassay supported is an enzyme-linked immunosorbent assay (ELISA).

63. The method of claim 61, wherein the immunoassay supported is a fluorescent immunoassay.

64. The method of claim 51, wherein detecting a measurable change in the second lightwave provides a diagnostic result.

65. The method of claim 51, further comprising conducting a real-time PCR reaction at the optical sensing site.

66. A kit for assaying a sample for a biologically active analyte comprising:
a scanning sensor system comprising a switchable light source, a detector, and a substrate coupled to and in optical communication with the switchable light source and the detector, wherein the substrate comprises a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection regions at each crossing, and a plurality of optical sensing sites each in optical communication with an intersection region;
packaging; and
instructions for use of the system.

67. The kit of claim 66, wherein the system comprises a planar lightwave circuit.

68. The kit of claim 66, wherein the crossing of the excitation waveguides and collection waveguides is substantially perpendicular.

69. The kit of claim 66, wherein the optical sensing sites comprise a sensor adapted to support an immunoassay, and wherein the kit further comprises one or more immunoassay reagents.

* * * * *

UNITED STATES PATENT AND TRADEMARK OFFICE
CERTIFICATE OF CORRECTION

| | | |
|---|---|---|
| PATENT NO. | : 7,951,583 B2 | Page 1 of 1 |
| APPLICATION NO. | : 11/683808 | |
| DATED | : May 31, 2011 | |
| INVENTOR(S) | : Duer | |

It is certified that error appears in the above-identified patent and that said Letters Patent is hereby corrected as shown below:

In Claim 10: Column 39, line 4:

Please insert --a-- before "surface";

In Claim 53: Column 41, line 9:

After "light wave," please insert --and--.

Signed and Sealed this
Twenty-third Day of August, 2011

David J. Kappos
*Director of the United States Patent and Trademark Office*